US012138154B2

(12) United States Patent
Moiso et al.

(10) Patent No.: US 12,138,154 B2
(45) Date of Patent: Nov. 12, 2024

(54) TWO-PART MITRAL VALVE AND IMPLANT METHOD

(71) Applicant: Corcym S.r.l., Milan (IT)

(72) Inventors: Silvano Moiso, Cocconato (IT); Felice Giuseppe Carlino, Borgomasino (IT); Paolo Monelli, Rivoli (IT); Monica Francesca Achiluzzi, Chivasso (IT)

(73) Assignee: Corcym S.r.l., Milan (IT)

( * ) Notice: Subject to any disclaimer, the term of this patent is extended or adjusted under 35 U.S.C. 154(b) by 421 days.

(21) Appl. No.: 17/454,043

(22) Filed: Nov. 8, 2021

(65) Prior Publication Data
US 2022/0054257 A1 Feb. 24, 2022

Related U.S. Application Data

(62) Division of application No. 16/309,063, filed as application No. PCT/IB2016/053515 on Jun. 15, 2016, now Pat. No. 11,173,026.

(51) Int. Cl.
*A61F 2/24* (2006.01)
(52) U.S. Cl.
CPC .......... *A61F 2/2409* (2013.01); *A61F 2/2412* (2013.01); *A61F 2/2427* (2013.01); *A61F 2220/0025* (2013.01); *A61F 2250/006* (2013.01)
(58) Field of Classification Search
CPC .............. A61F 2/2409; A61F 2250/006; A61F 2220/0008; A61F 2220/0025
USPC ........................................................ 623/2.4
See application file for complete search history.

(56) References Cited

U.S. PATENT DOCUMENTS

| 4,680,031 A | 7/1987 | Alonso |
| 6,106,550 A | 8/2000 | Magovern |
| 6,468,305 B1 | 10/2002 | Otte |
| 2003/0023302 A1 | 1/2003 | Moe et al. |

(Continued)

FOREIGN PATENT DOCUMENTS

| CN | 101180010 A | 5/2008 |
| DE | 202011000848 U1 | 6/2011 |

(Continued)

OTHER PUBLICATIONS

International Search Report and Written Opinion for International Application No. PCT/IB2016/053515, mailed Feb. 20, 2017, 14 pages.

*Primary Examiner* — Brian E Pellegrino
(74) *Attorney, Agent, or Firm* — Crowe & Dunlevy LLC

(57) ABSTRACT

In certain embodiments, a multiple component heart valve prosthesis includes an abutment ring and a removable bioprosthetic heart valve. The abutment ring is configured for attachment at a heart valve annulus location and includes a locking system. The removable bioprosthetic heart valve includes a valve frame and at least one locking feature. The at least one locking feature is configured to be received by the locking system. The bioprosthetic heart valve can be rotated relative to the abutment ring such that the at least one locking feature transitions from a disengaged position to a first engaged position. When in the disengaged position the bioprosthetic heart valve may be removed from the abutment ring, and when rotated to the engaged position the bioprosthetic heart valve is restrained from axial movement relative to the abutment ring.

18 Claims, 17 Drawing Sheets

(56) References Cited

U.S. PATENT DOCUMENTS

| | | | |
|---|---|---|---|
| 2004/0044406 A1* | 3/2004 | Woolfson | A61F 2/2409 |
| | | | 623/2.11 |
| 2007/0179604 A1* | 8/2007 | Lane | A61F 2/2409 |
| | | | 623/2.38 |
| 2014/0052244 A1* | 2/2014 | Rolando | A61F 2/2409 |
| | | | 623/2.37 |
| 2016/0067042 A1 | 3/2016 | Murad et al. | |

FOREIGN PATENT DOCUMENTS

| | | | | |
|---|---|---|---|---|
| EP | 0095970 A2 | 12/1983 | | |
| EP | 3034014 A2 | 6/2016 | | |
| JP | 2004154164 A | 6/2004 | | |
| WO | WO-9804213 A1 * | 2/1998 | | A61F 2/2409 |
| WO | WO-0203892 A1 * | 1/2002 | | A61F 2/2409 |
| WO | WO-2006127756 A2 | 11/2006 | | |
| WO | WO-2010112608 A1 | 10/2010 | | |
| WO | WO-2012110767 A2 | 8/2012 | | |

\* cited by examiner

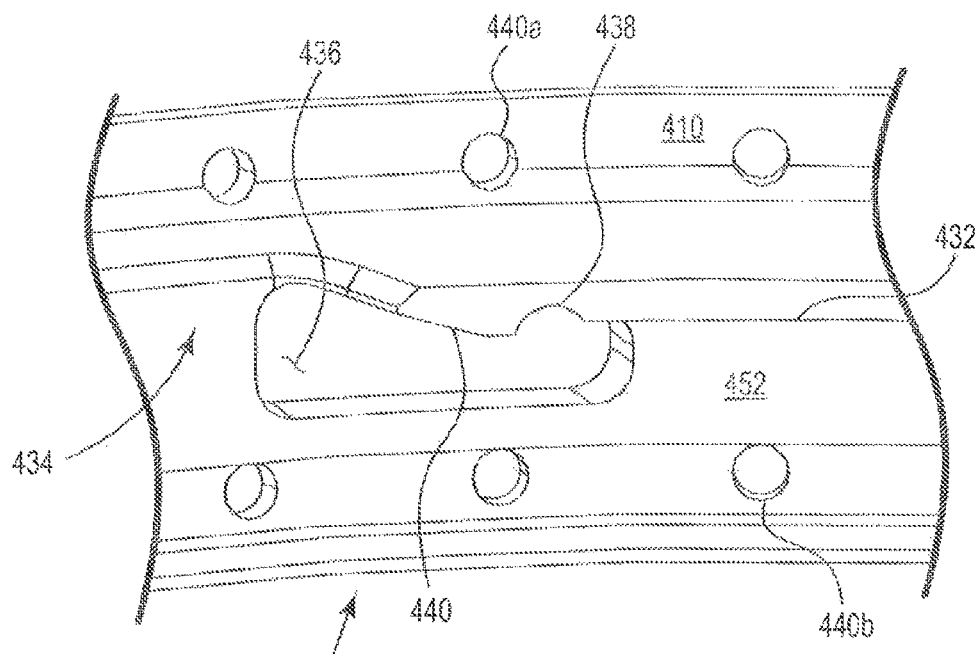
Fig. 3A - DETAIL
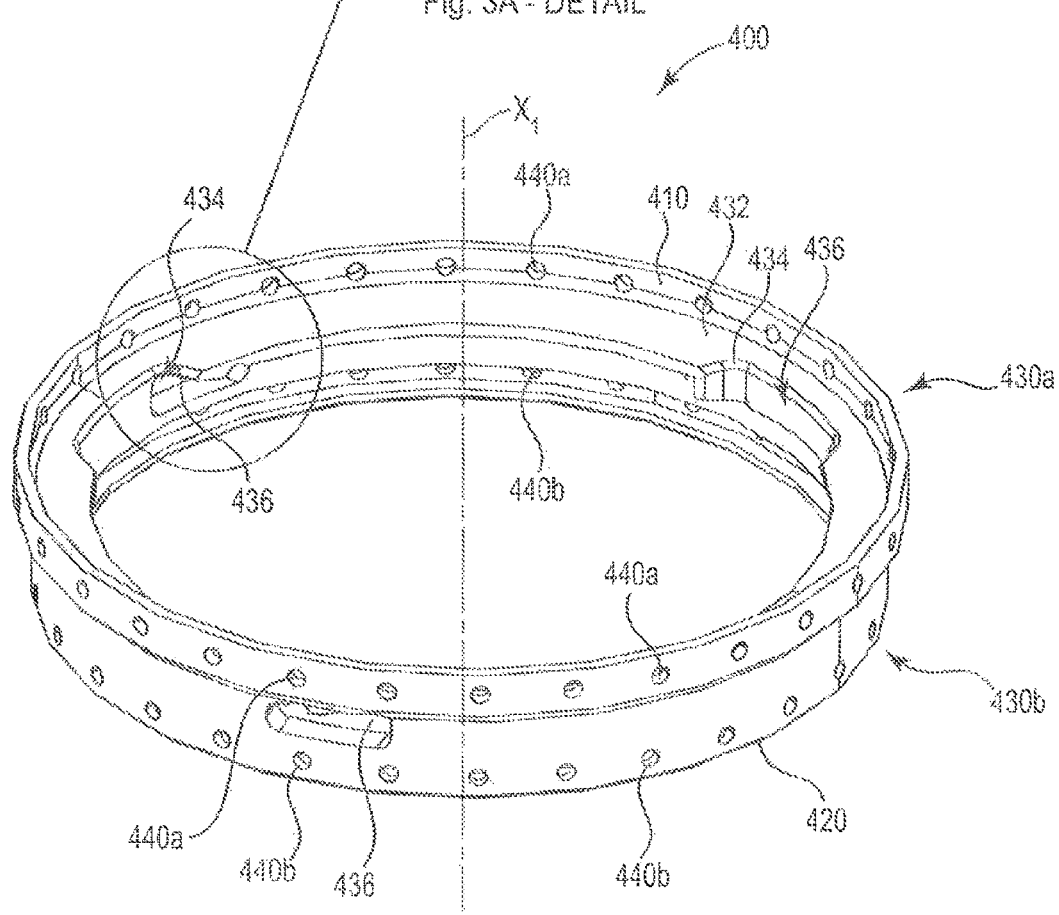
Fig. 3A

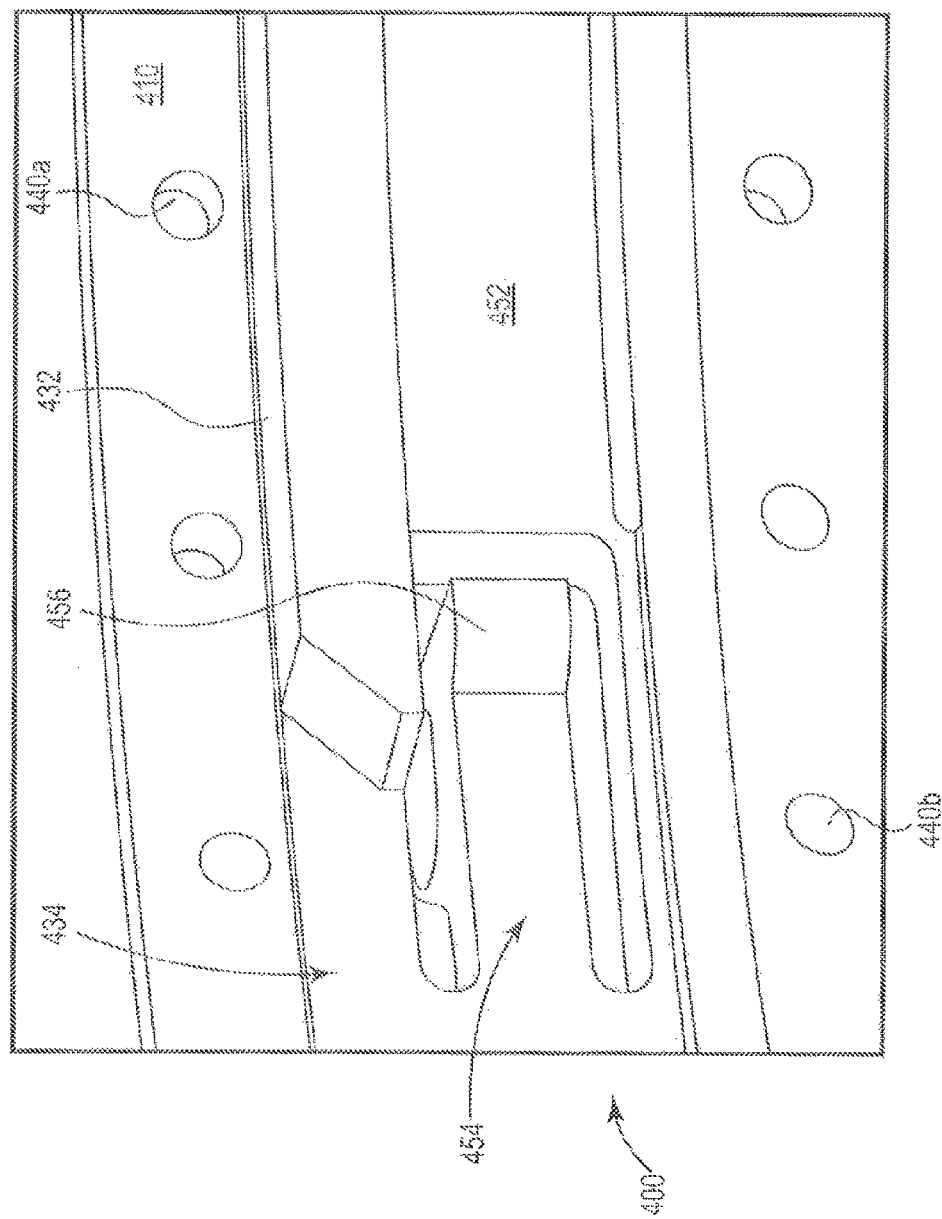

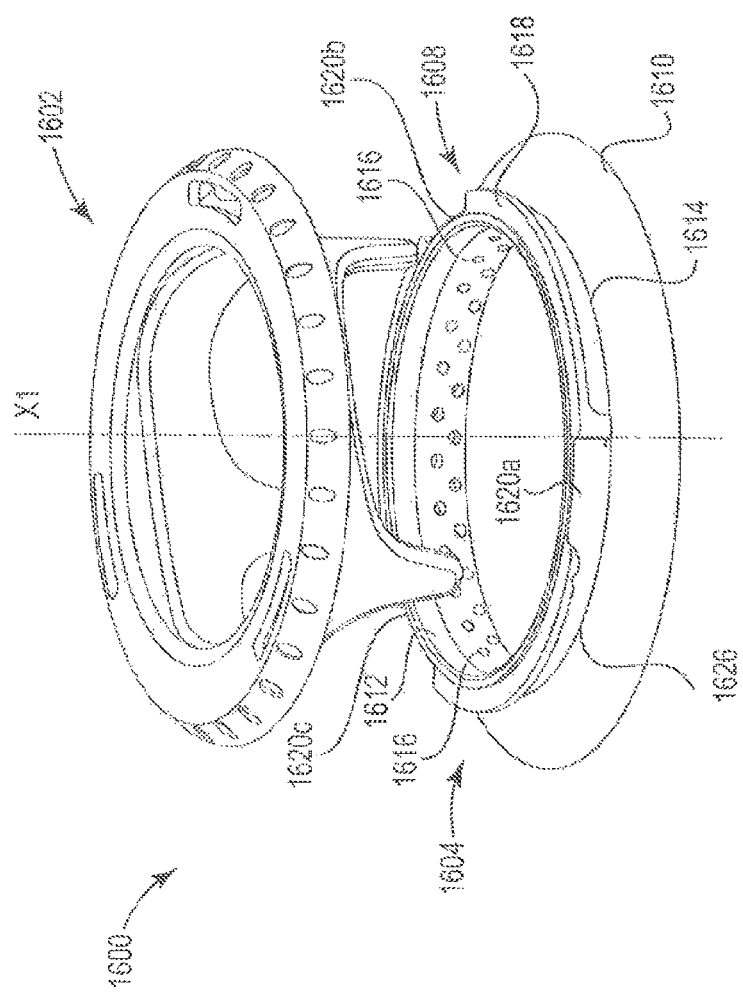

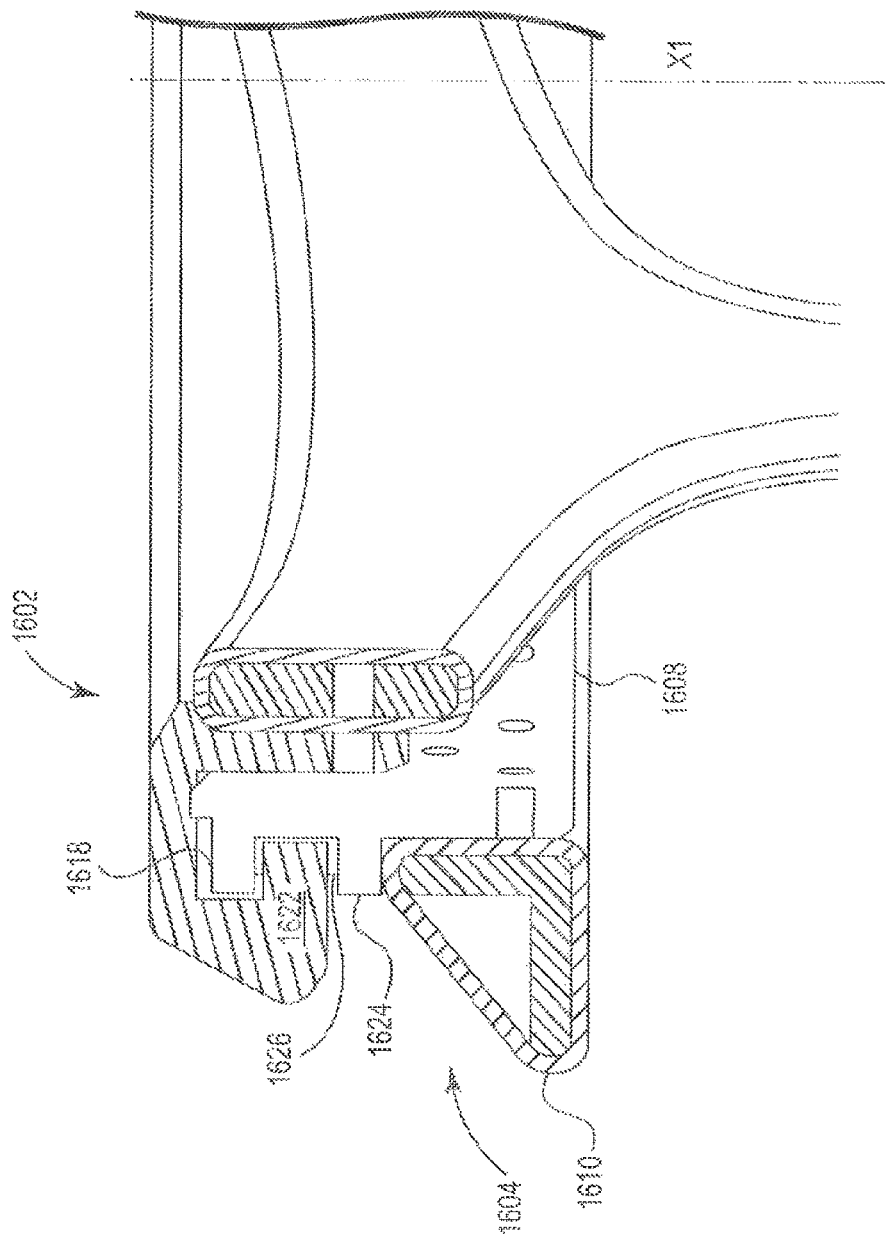

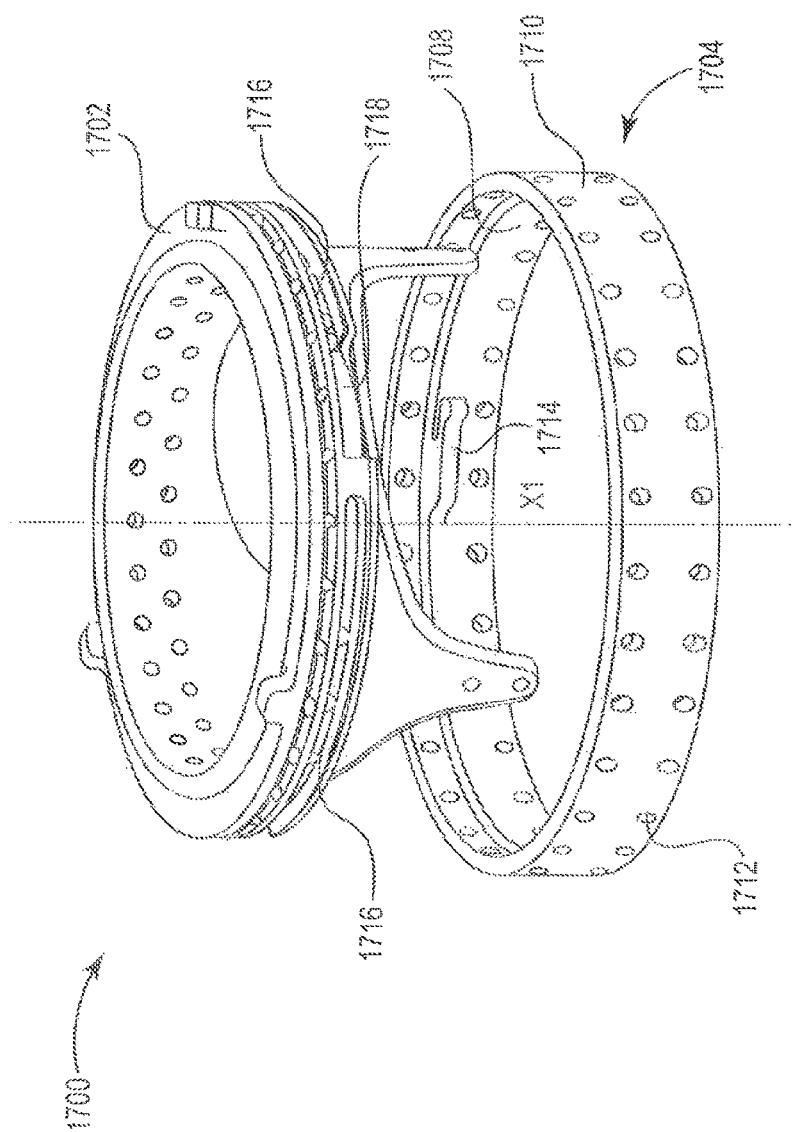

TWO-PART MITRAL VALVE AND IMPLANT METHOD

CROSS-REFERENCE TO RELATED APPLICATION

This application is a divisional application of U.S. patent application Ser. No. 16/309,063, filed Dec. 11, 2018, now U.S. Pat. No. 11,173,026, which is a national stage application of PCT/IB2016/053515, filed Jun. 15, 2016, the disclosures of each of which are herein incorporated by reference in their entireties.

TECHNICAL FIELD

The present disclosure elates generally to a prosthetic mitral valve and implant method.

BACKGROUND

Prosthetic heart valves can replace defective human valves in patients. Prosthetic heart valves come in two varieties: bioprosthetic heart valves and mechanical heart valves. During a valve replacement procedure, valve prostheses are typically sutured to peripheral tissue of a natural heart valve orifice (the "annulus") after surgical removal of damaged or diseased natural valve structure. For example, the sewing ring of the prosthetic valve may be secured to the annulus via sutures. This procedure can be very complicated, as surgeons are manipulating multiple sutures and small components while working in tight spaces with limited visibility. The difficulties can be even greater with the implementation of tissue valves, given their shape and construction.

When placing a bioprosthetic heart valve in a mitral position, for example, the commissure posts are the first portion of the valve entering inside the patient's annulus during valve delivery. Given the close proximity of the multiple pre-installed sutures and the commissure posts, it is not uncommon for one or more of the commissure posts to become entangled with one or more of the pre-installed sutures. Moreover, as the commissure posts are not visible at this point during the procedure, the surgeon cannot visually detect whether any such entanglement has occurred. This problem is even more pronounced during a minimally-invasive access approach, a technique that is quickly becoming more common in the industry, which provides even more limited visibility of the surgical field during valve delivery.

An entanglement between the commissure posts and the sutures typically leads to "suture looping," a situation where one or more of the sutures used to attach the valve to the valvular ring is inadvertently wrapped around one or more of the commissure post tips. When this occurs, the looped suture can interfere with the implant procedure. Worse yet, a looped suture can disrupt valve operation and prevent proper coaptation of the valve leaflets, or possibly even damage one or more of the tissue leaflets.

Attempts have been made to overcome this "suture looping" problem. Some designs have incorporated specially designed mechanisms to constrict the commissure posts inwardly prior to implantation—the "cinch" system. Other designs have incorporated a combination of a cinch system and a series of flexible threads extending in a taut fashion across the outflow end of the valve to occlude the commissure posts of the valve—the "anti-looping" system. Both approaches minimize but do not completely eliminate the risk of suture looping. Additionally, because the cinch system and anti-looping system are located on the outlet side of the valve—which the surgeon cannot see—neither approach offers the surgeon the ability to visually detect whether or not suture looping has occurred.

Accordingly, there remains a need for improvements in prosthetic heart valve assemblies and components that facilitate the initial implantation, manipulation, and replacement of implanted prosthetic heart valve mechanisms. There also remains a need for a system and method of implanting heart valve prostheses and suture rings that reduces the time and risks of implantation, thereby increasing patient well-being and outlook.

SUMMARY

The embodiments disclosed herein provide a multi-component heart valve prosthesis comprised of a sewing ring element and a separable tissue valve element. Moreover, the embodiments disclosed herein include a novel bioprosthetic heart valve implantation procedure, including the steps of first suturing to the patient's valvular rim the sewing element, and second installing the valve, element within the secured sewing ring element. Further, embodiments provide for a multi-component heart valve in which the two elements are designed to allow rotation of the valve element with respect to the sewing ring element after the latter is sutured to the annulus, thus giving the surgeon the possibility to fine tune the valve commissural post locations after valve placement.

In Example 1, a multiple component heart valve prosthesis includes an abutment ring and a removable bioprosthetic heart valve. The abutment ring is configured for attachment at a heart valve annulus location and includes a locking system. The removable bioprosthetic heart valve includes a valve frame and at least one locking feature. The at least one locking feature is configured to be received by the locking system. The bioprosthetic heart valve can be rotated relative to the abutment ring such that the at least one locking feature transitions from a disengaged position to a first engaged position. When in the disengaged position the bioprosthetic heart valve may be removed from the abutment ring, and when rotated to the engaged position the bioprosthetic heart valve is restrained from axial movement relative to the abutment ring.

In Example 2, the heart valve prosthesis of Example 1, wherein the locking system of the abutment ring includes at least one channel.

In Example 3, the heart valve prosthesis of Example 2, wherein the at least one channel is configured to accept the at east one locking feature of the removable bioprosthetic heart valve such that the removable bioprosthetic heart valve can be rotated relative to the abutment ring.

In Example 4, the heart valve prosthesis of any of Examples 1-3, wherein the locking system of the abutment ring includes a spring-like structure.

In Example 5, the heart valve prosthesis of Example 4, wherein the spring-like structure is a clip.

In Example 6, the heart valve prosthesis of Example 2, wherein the channel is positioned on an exterior surface of the abutment ring.

In Example 7, the heart valve prosthesis of any of Examples 1-6, wherein when positioned in the first engaged position, the removable bioprosthetic heart valve remains free to be rotated relative to the abutment ring from the first engaged position to a second engaged position.

In Example 3, the heart valve prosthesis of any of Examples 1-7, wherein a torque exceeding a first rotational threshold is required to cause the removable bioprosthetic heart valve to be rotated relative to the abutment ring.

In Example 9, the heart valve prosthesis of any of Examples 1-8, wherein the locking system of the abutment ring includes a plurality of channels.

In Example 10, the heart valve prosthesis of any of Examples 1-9, wherein the removable bioprosthetic heart valve includes a plurality of locking features.

In Example 11, the heart valve prosthesis of any of Examples 1-10, further comprising a static locking feature configured to secure the removable bioprosthetic heart valve within the abutment ring once positioned in a desired position such that the removable bioprosthetic heart valve is prevented from being further rotated relative to the abutment ring.

In Example 12, the heart valve prosthesis of any of Examples 1-11, wherein the abutment ring is attachable to a patients mitral valve rim.

In Example 13, the heart valve prosthesis of any of Examples 1-12, wherein the locking system includes at least one locking feature cavity.

In Example 14, wherein the at least one locking feature comprises a boss.

In Example 15, a multiple-component, heart valve prosthesis includes an abutment ring and a removable bioprosthetic heart valve. The abutment ring is configured for attachment at a heart valve annulus and includes a locking system having at least one locking feature cavity and least one locking feature channel. The removable bioprosthetic heart valve includes a valve frame and at least one locking feature. The looking features is configured to be received by the locking feature cavity to a first, disengaged position, and rotated from the first, disengaged position to a first, engaged position in which the bioprosthetic heart valve is restrained from axial movement related to the abutment ring.

In Example 16, heart valve prosthesis of Example 15, wherein when positioned in the first engaged position, the removable bioprosthetic heart valve remains free to be rotated relative to the abutment ring frog the first, engaged position to a second, engaged position.

In Example 17, heart valve prosthesis of any of Examples 15-16, wherein a torque exceeding a first rotational threshold is required to cause the removable bioprosthesis heart valve to be rotated relative, to the abutment ring.

In Example 18, a method for implanting a multiple component heart valve prosthesis includes securing an abutment ring to a heart valve annulus of a patient's heart, the abutment ring comprising a locking system, inserting a removable bioprosthetic heart valve into the abutment ring such that at least one locking feature of the bioprosthetic heart valve is received by the locking system to a first disengaged position, and rotating the removable bioprosthetic heart valve relative to the abutment ring from the first disengaged position to a first engaged position. The removable bioprosthetic heart valve may be freely removed from the abutment ring in the first disengaged position, and when rotated to the first engaged position, the removable bioprosthetic heart valve is prohibited from axial movement with relative the abutment ring.

In Example 19, a multiple component heart valve prosthesis includes a removable bioprosthetic heart valve and an abutment ring. The removable bioprosthetic heart valve includes a valve frame and a locking system. The abutment ring is configured for attachment at a heart valve annulus location and includes at least one locking feature. The at least one locking feature is configured to be received by the locking system. The bioprosthetic heart valve can be rotated relative to the abutment ring such that the at least one locking feature transitions from a disengaged position to a first engaged position. When in the disengaged position the bioprosthetic heart valve may be removed from the abutment ring, and when rotated to the engaged position, the bioprosthetic heart valve is restrained from axial movement relative to the abutment ring.

In Example 20, the heart valve prosthesis of Example 19, wherein the locking system is positioned on an exterior face of the valve frame, and wherein the at least one locking feature is positioned on an interior face of the abutment ring.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 3A is a perspective view illustrating a valve retention ring, according to some embodiments described in the disclosure.

FIG. 3B is a perspective view illustrating a portion of a valve retention according to some embodiments described in the disclosure.

FIG. 8 is a partially exploded view of a bioprosthetic heart valve system, according to some embodiments described in the disclosure.

FIG. 10 is a cross-sectional side view of a portion of the bioprosthetic heart valve system of FIG. 8.

FIG. 11 is a partially exploded view of an implantable abutment ring and a valve frame, according to some embodiments described in the disclosure.

Figure 1:
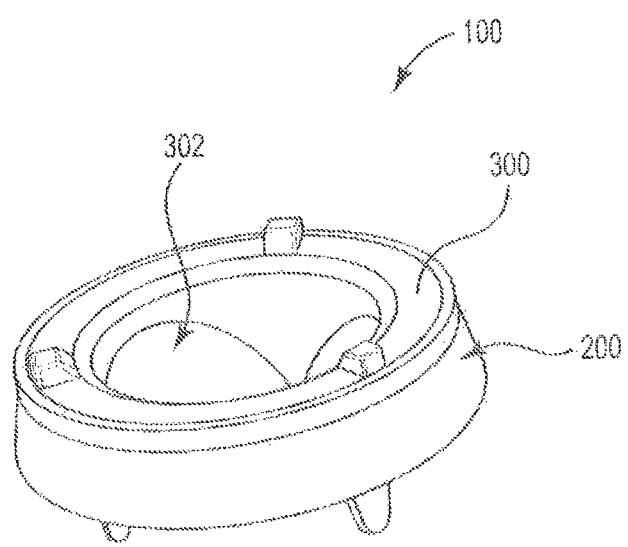
FIG. 1 is a perspective view illustrating a bioprosthetic heart valve system, according to some embodiments described in the disclosure.

While the invention is amenable to various modifications and alternative forms, specific embodiments have been shown by way of example in the drawings and are described in detail below. The intention, however, is not to limit the invention to the particular embodiments, but is intended to cover all modifications, equivalents, and alternatives falling within the scope of the invention as defined by the appended claims.

DETAILED DESCRIPTION

The present device and method can be utilized to improve implantation procedures and performance of heart valve prostheses in a wide variety of applications where the heart valve prosthesis is surgically attached to a prepared valvular rim (or annulus). The embodiments disclosed herein are directed to improved removable bioprosthetic heart valves comprising an implantable abutment ring and a valve frame having tissue leaflets attached thereto (or alternatively, a mechanical pivotal disk or mechanical leaflets or equivalents thereof). The various aspects of the present invention may be utilized in mitral valve (or other heart valve—aortic, etc.) replacement wherein a prosthetic heart valve frame operates in accordance with a suture ring.

FIGS. 1 and 2 illustrate an example embodiment of an implantable prosthetic heart valve assembly 100. In various embodiments, the implantable prosthetic heart valve assembly 100 is a bioprosthetic (i.e., tissue) heart valve assembly. As discussed above, tissue valves generally include a plurality of tissue cusps or leaflets, e.g., made from bovine pericardium or harvested porcine heart valve tissue, mounted onto a stationary metal or plastic frame structure. This frame structure operates to maintain the various cusps or leaflets in a desired orientation and shape that promotes sufficient valve opening and closing characteristics and proper blood flow.

In various other embodiments, the prosthetic heart valve assembly 100 is a mechanical heart valve assembly. As mentioned above, a modern mechanical heart valve prosthesis is typically formed of an annular valve seat in a relatively rigid valve body and includes an occluding disk or pair of leaflets that moves between a closed, seated position and an open position in a prescribed range of motion.

While the embodiments discussed herein can operate to employ either bioprosthetic or mechanical heart valves, the discussion below is provided with reference to bioprosthetic heart valves. It should be appreciated, however, that mechanical heart valves may also be employed with the embodiments discussed herein, and that reference to bioprosthetic heart valves should not serve to limit the scope of this disclosure.

In one embodiment, an implantable prosthetic heart valve assembly 100 includes an implantable abutment ring 200 and a valve frame 300. As discussed in greater detail below, abutment ring 200 is configured to receive valve frame 300, and valve frame 300 is configured to be received by abutment ring 200. Together, abutment ring 200, valve frame 300, and a plurality of tissue leaflets 302 (located within the valve frame 300) generally make up the structure of the implantable prosthetic heart valve assembly 100.

Figure 2A:
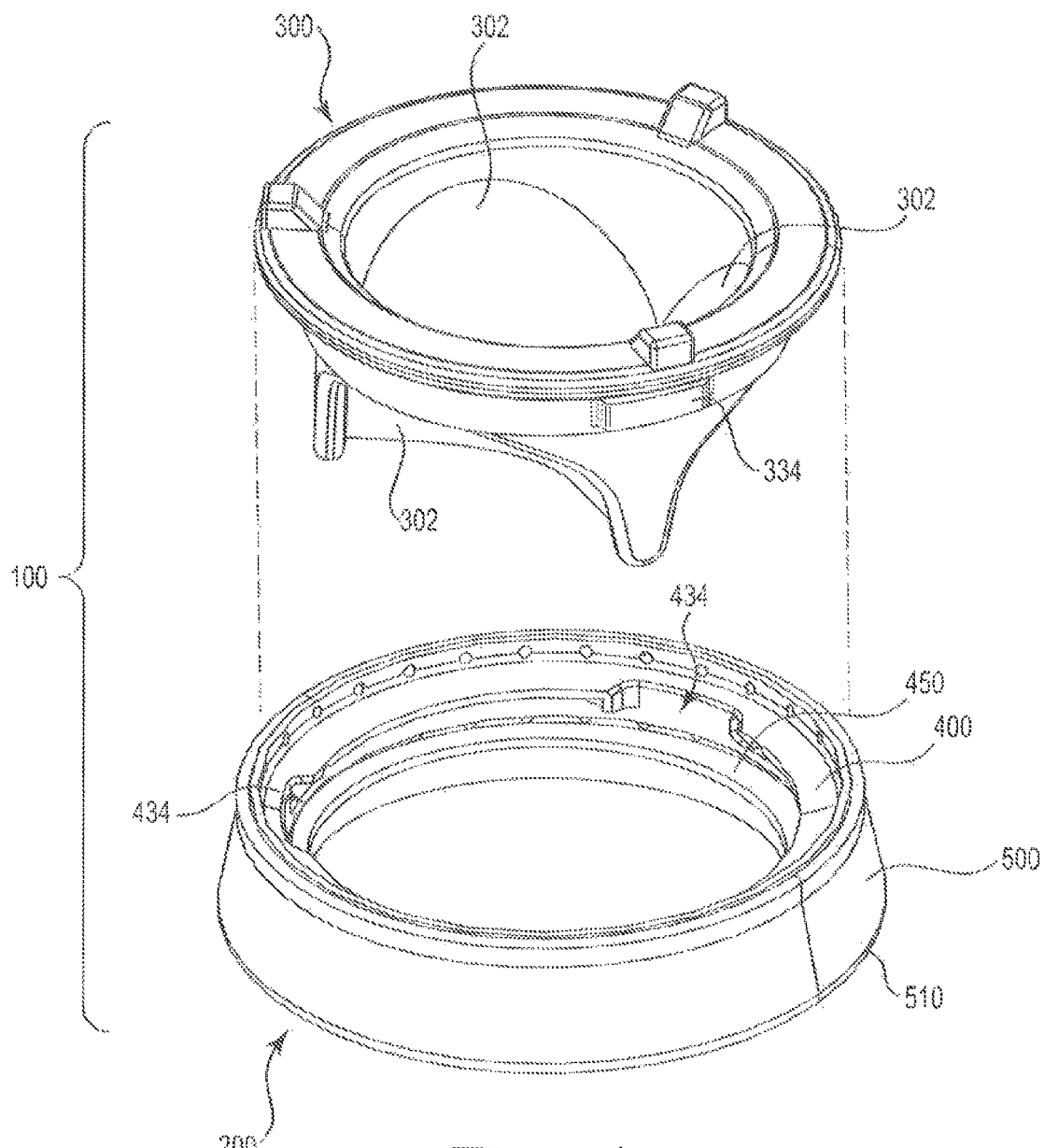
FIG. 2A is a partially exploded view of the bioprosthetic heart valve system of FIG. 1, according to some embodiments described in the disclosure.
Figure 2B:
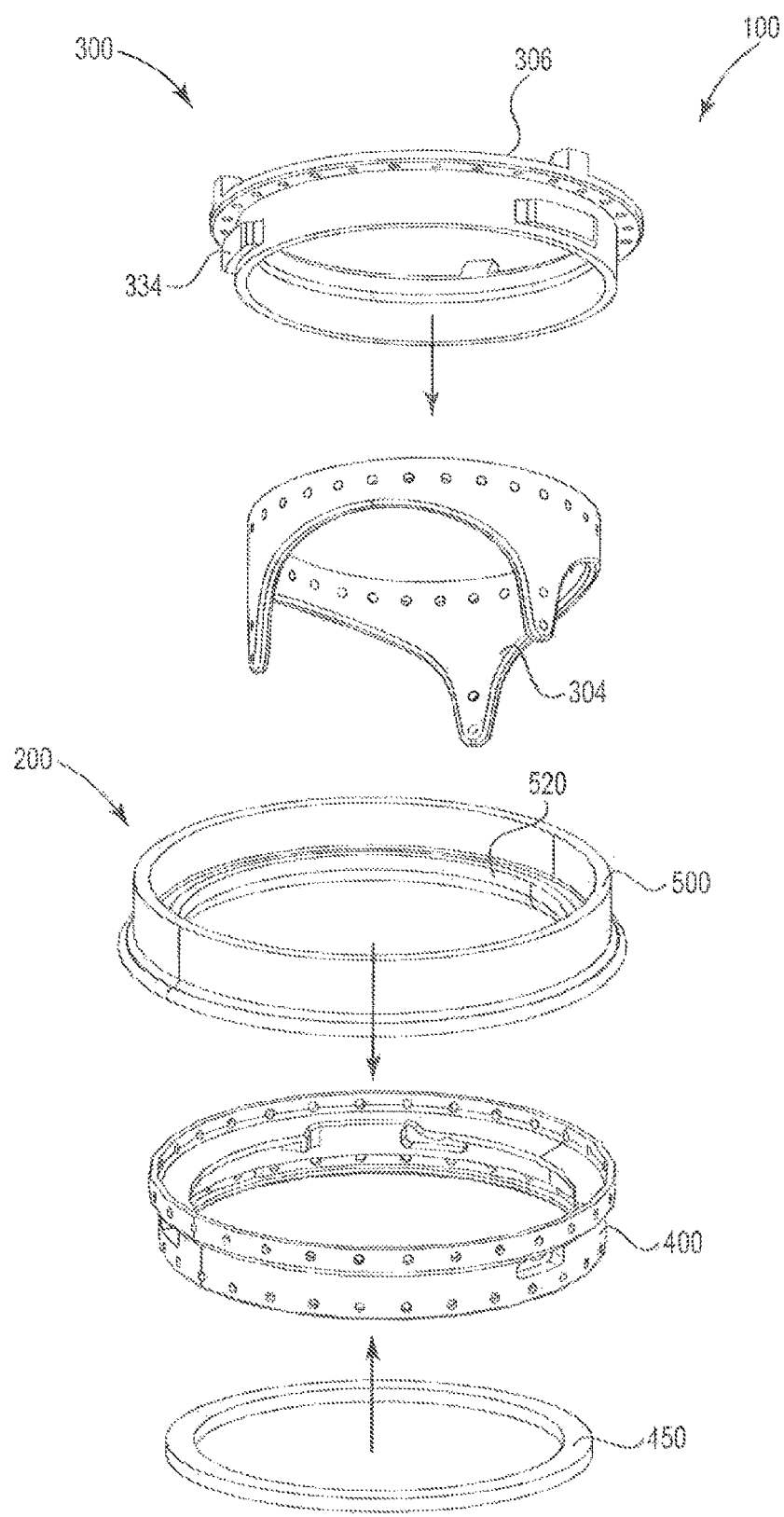
FIG. 2B is a partially exploded view of an implantable abutment ring and a valve frame shown in FIG. 2A.
Figure 2C:
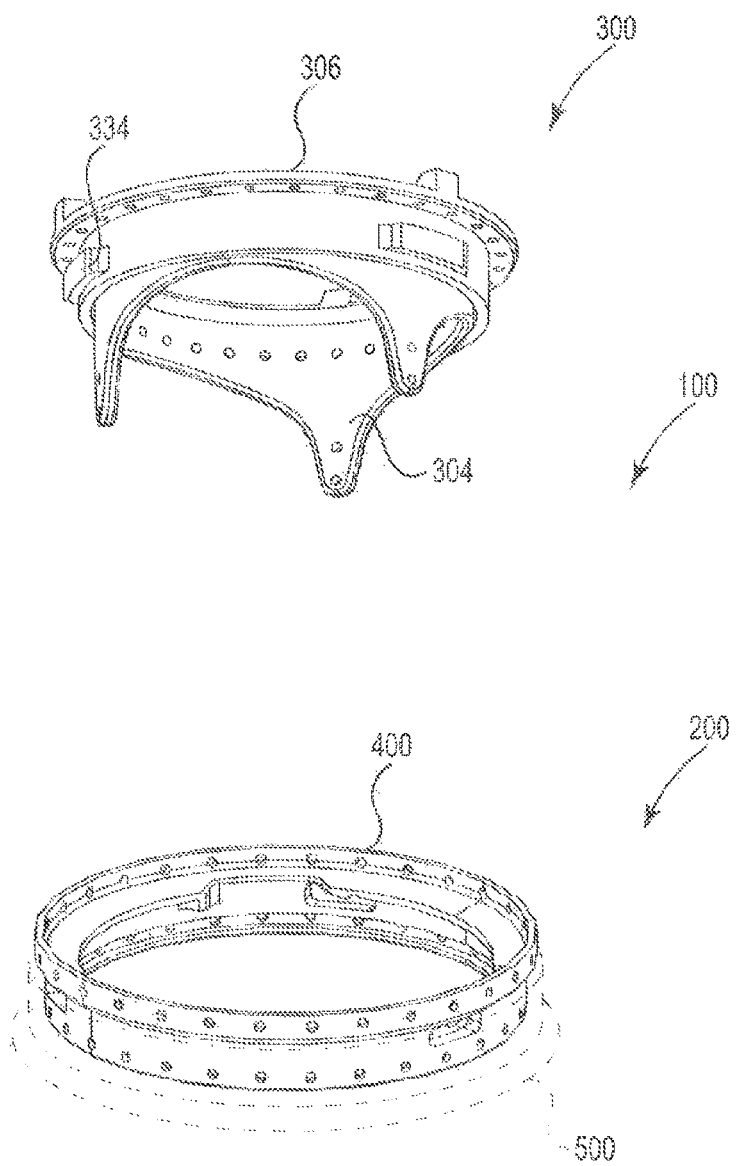
FIG. 2C is a partially exploded view of the bioprosthetic heart valve system of FIG. 1.

FIG. 1 illustrates the implantable prosthetic heart valve assembly 100 in its assembled configuration. FIGS. 2A and 2C illustrate the implantable heart valve assembly 100 of FIG. 1 in a partially exploded view, which shows how valve frame 300 may fit within abutment ring 200. FIG. 2B illustrates an exploded view of the abutment ring 200 and the valve frame 300. In one embodiment, abutment ring 200 includes a valve retention ring 400 and a suture ring 500. In some embodiments, a washer 450 may also be used with valve retention ring 400 to limit certain axial movement of the valve frame 300 relative to the abutment ring 200 and also to assist with sealing. The washer 450 may be positioned within the valve retention ring 400. Washer 450 is ring-shaped with a hollow interior. In some embodiments, the suture ring 500 includes a lip 520 that extends radially inward. Like the washer 450, the lip may be used with valve retention ring 400 to limit certain axial movement of the valve frame 300 relative to the abutment ring 200 and also to assist with sealing.

In one embodiment, valve retention ring 400 is ring shaped (or cylindrically shaped) with a hollow interior. For example, as shown in FIG. 3A, valve retention ring 400 is in the shape of a ring and has a central axis X1. Valve retention ring 400 (shown without washer 450) has an interior face 410, an exterior face 420, an upper portion 430a, and a lower portion 430b. In some embodiments, as discussed above, valve retention ring 400 includes one or more features which provide for fastening valve retention ring 400 to suture ring 500. As illustrated in FIG. 3A, a plurality of apertures 440 (such as upper apertures 440a and lower apertures 440b) are positioned along each of the circumferential perimeters of the upper and lower portions 430a and 430b. In the embodiment illustrated in FIG. 3A, each aperture 440a,b extends from the interior face 410 to the exterior face 420 such that each aperture's axis extends generally perpendicular relative to axis X1 of the valve retention ring 400.

In one embodiment, valve retention ring 400 includes a ledge 432 extending from the interior face 410 towards the central axis X1. The ledge 432 includes a plurality of openings or cutaway portions 434 about the central axis X1. The plurality of openings 434 have locations and shapes in order to allow a plurality of corresponding locking features 334 on the exterior of the valve frame 300 (FIGS. 2A-C) to pass through the plurality of openings 434 to form a seating structure for frame 300 within valve retention ring 400. The valve frame 300 is configured to be assembled to the valve retention ring 400 by inserting the locking features 334 of the valve frame 300 through the plurality of corresponding openings 434 of the ledge 432. The valve frame 300 is further configured to be retained in the valve retention ring 400 by rotating the valve frame 300 to cause the locking features 334 to travel along and below the ledge 432 and within a channel 452 on the valve retention frame 400. For example, the channel 452 may be formed between an upper ledge (e.g., ledge 432) and a lower edge. Valve frame 300 may be rotated until coking features 334 are aligned with a plurality of orifices 436 that extend through the valve retention ring 400. In some embodiments, locking features 334 may fit within the orifices 436 (e.g., by a snap-fit) such that the engagement of the locking features 334 within the orifices 436 secures the valve frame 300 and ring 400 together as a single unit.

As shown in inset A of FIG. 3A, in some embodiments, the ledge 432 of the valve retention ring 400 includes a recess 438 along a bottom side of the ledge 432. The ledge 432 also includes a sloped surface 440 that extends to the recess 438. When the valve frame 300 is rotated, the locking features 334 travel long the sloped surface 440 towards the recess 438 and into the channel 452. The locking features 334 or at least a portion of the locking features 334 engage or snap into the recess 438 such that the locking features 334 cannot rotate past the recess 433. For example, the locking features 334 can includes a boss or protrusion that include at least one surface that is shaped to engage with the recess 438 such that the valve frame 300 maintains its rotational position with respect to the valve retention ring 400. In some embodiments, the recess 438 is shaped as a half-spherical recess, and the protrusion includes a surface shaped as a half-spherical protrusion, which fits into the recess 438.

In another embodiment, the valve frame 300 is configured to be assembled to the valve retention ring 400 by inserting the locking features 334 of ledge 432 through the plurality of corresponding openings 434 of the valve retention ring 400. As shown in FIG. 3B, the valve frame 300 is further configured to be retained in the valve retention ring 400 by rotating the valve frame 300 to cause the locking features 334 to rotate towards (and into) a channel 452 formed below the ledge 432. When the valve frame 300 is rotated, the locking features 334 of the frame 300 travel along locking features 454 of the valve retention ring 400, which in the embodiment of FIG. 3B includes a sloped structure 456 that extends radially inward. The locking features 454 are shown as being integrally formed with the valve retention ring 400. As the locking features 334 of the valve frame 300 contact the locking features 454 and structure 456 of the valve retention ring 400, the locking features 454 are urged radially outward. Once the locking features 334 rotate past the structure 456, the locking features 454 return (e.g., snap) to their initial position such that the locking features 334 cannot rotate back past the locking features 454. The locking features 334 may, however, rotate within the channel 452.

Figure 3C:
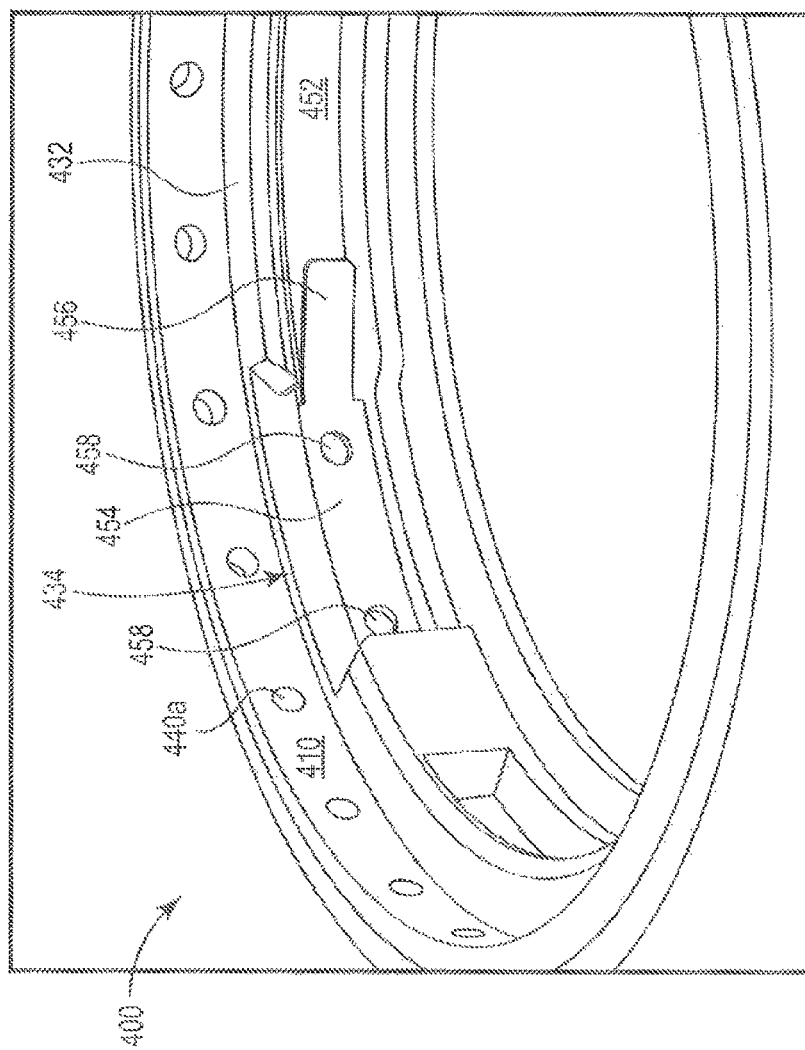
FIG. 3C is a perspective view illustrating a portion of a valve retention ring, according to some embodiments described in the disclosure.

FIG. 3B shows the locking features 454 of the valve retention ring 400 as being integral with the valve retention ring 400, but it will be appreciated that other approaches may readily be employed. For example, FIG. 3C shows an embodiment where locking features 454 are a separate part coupled to the valve retention ring 400. In FIG. 3C, the valve retention ring 400 includes locking features 454 comprising a clip that may be coupled to the ring 400. The clip includes a spring-like structure 456. Like the embodiment shown in FIG. 3B, the valve frame 300 is configured to retained in the valve retention ring 400 by rotating the valve frame 300 to cause the locking features 334 to rotate into a channel 452 formed below the ledge 432. As the locking features 334 of the valve frame 300 travel along locking features 454 and spring-like structure 456, the locking features 334 press against the spring-like structure 456 and move the structure radially outward until the locking features 334 rotate past the spring-like structure 456—upon which the spring-like structure 456 returns (e.g., springs, snaps) to its initial position. Once the spring-like structure 456 returns to its initial position, the locking features 334 cannot rotate back past the locking features 454 although the locking features 334 may rotate within the channel 452. It will be appreciated that other spring-like structures and positions may readily be employed and may comprise materials such as metal, silicon, plastic, among others. In some embodiments, the spring-like structure 456 may flex in an axial direction as the locking features 334 travel along the spring-like structure 456. In some embodiments, the spring-like structure 456 may be positioned within the openings 434 of the valve retention ring 400. As the locking features 334 are inserted into and travel along the openings 434, the looking features 334 press against the spring-like structure 456 to deflect the structure. In some embodiments, locking features 454 may be unlocked (e.g., by use of a tool to manually depress spring-like structure 456) to permit removal of the valve frame 300 from the valve retention ring 400, even after locking features have been rotated into channel 452. By unlocking locking features 454, the valve may be rotated such that locking features 334 return to alignment with the openings 434 in channel 432, thereby permitting removal of the valve from the valve retention ring 400.

Valve retention ring 400 is generally formed of a biocompatible metal (e.g., titanium, stainless steel, or other suitable metal alloy), a plastic material (e.g., acetal homopolymer plastic), reinforced pyrolytic carbon, or any other suitable biocompatible material.

Referring back to FIGS. 2A-C, in certain embodiments, suture ring 500 is made of a suture permeable fabric 510 comprised of a woven synthetic fiber capable of accepting of tissue ingrowth. For example, suture permeable fabric can be made of polyester (polyethylene terephthalate) or polytetrafluoroethylene (PTFE). In some embodiments, the suture permeable fabric 510 may also be filled with a biocompatible material, such as silicone, silicone rubber, polyurethane, or a hydrogel. In some embodiments, the suture permeable fabric 510 may be coated with a thin layer of pyrolytic carbon to improve biocompatibility. The suture ring 500 may thus be formed and shaped as desired.

Suture ring 500 may be ring (or cylindrically) shaped, or may adopt other anatomically compatible shapes, e.g., a D-shaped structure more commonly used in annuloplasty rings. Suture ring 500 is configured to circumferentially engage or cover, partially or fully, valve retention ring 400, and be attached thereto (as discussed below). In one embodiment, an interior surface of the suture ring 500 (not illustrated) is sized and shaped to engage, the exterior surface 420 of valve retention ring 400.

In various embodiments, valve retention ring 400 and suture ring 500 (FIGS. 2A-C) are coupled together and comprise a single unit. That is, in certain embodiments, valve retention ring 400 and suture ring 500 are fastened together prior to being implanted into a patient. In one such embodiment, suture ring 500 and valve retention ring 400 and are stitched together, e.g., by sutures through a plurality of apertures 440a, 440b and suture permeable fabric 510, in one exemplary embodiment. In yet another embodiment, some other suitable method (e.g., rivets or pins) is employed to couple valve retention ring 400 and suture ring 500 to form abutment ring 200.

As discussed above, in various embodiments, the abutment ring 200 is configured to receive valve frame 300. As it in FIGS. 2A-C, valve frame 300 includes a frame structure 304 and a plurality of tissue leaflets 302. Valve frame 300 is generally formed of a biocompatible metal (e.g., titanium, stainless steel, or other suitable metal alloy), a plastic material (e.g., acetal homopolymer plastic), reinforced pyrolytic carbon, or of any other suitable biocompatible material. The frame structure 304 is coupled to a ring-like structure 306 from which the locking features 334 extend or are positioned on. Although shown as distinct elements in FIGS. 2B and 2C, in some embodiments, the frame structure and ring-like structure may comprise an integral frame/ring element.

Figure 4:
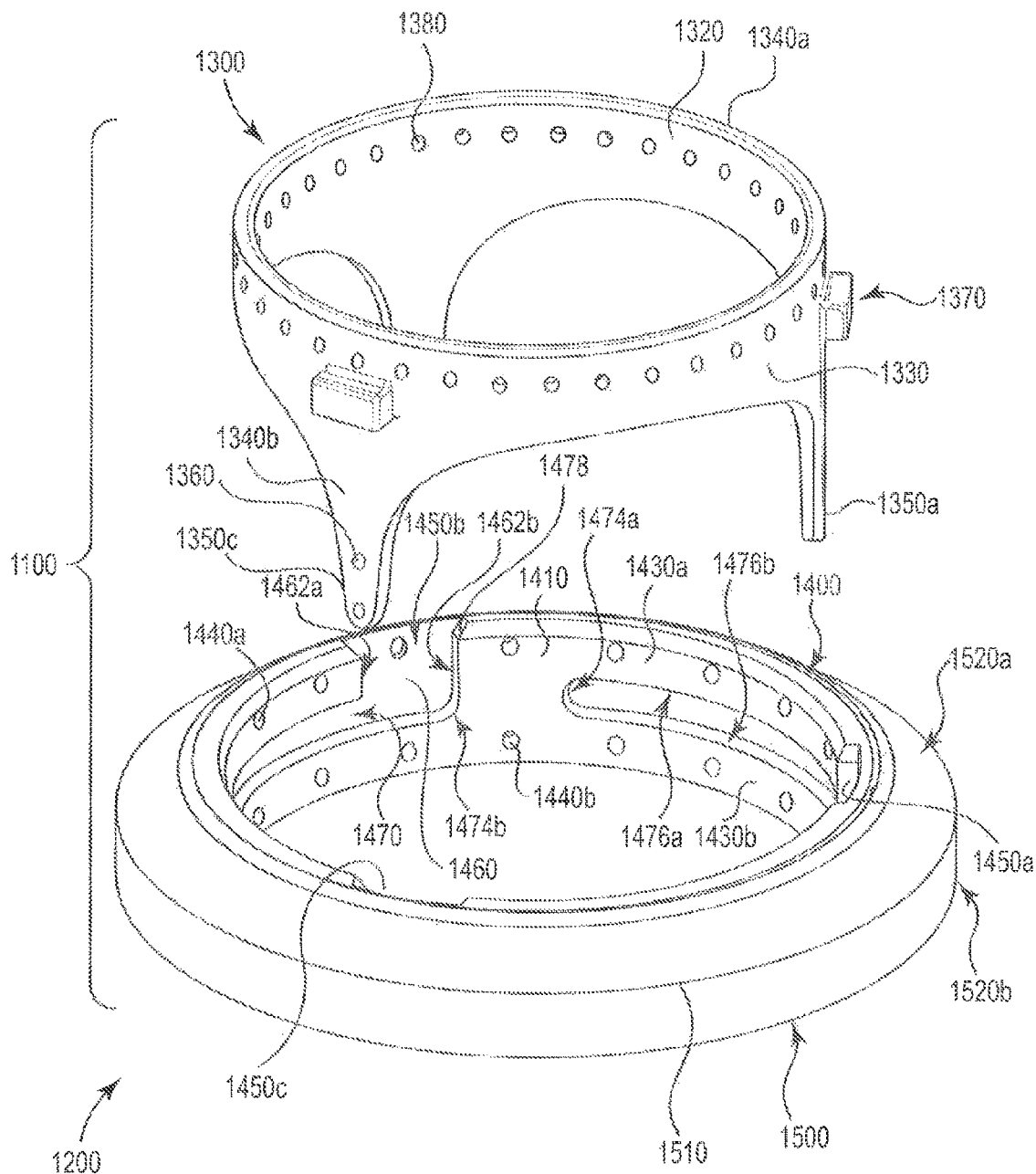
FIG. 4 is a partially exploded view of another embodiment of the bioprosthetic heart valve system, according to some embodiments described in the disclosure.

FIG. 4 illustrates another embodiment of an implantable prosthetic heart valve assembly 1100 in a partially exploded view. The figure shows how valve frame 1300 (shown without leaflets, but contemplated to include leaflets) may fit within an abutment ring 1200.

As shown in FIG. 4, suture ring 1500 includes an upper portion 1520a and a lower portion 1520b. In certain embodiments, the lower portion 1520b is configured to be sutured (or fastened via another suitable manner) to a patient's prepared annulus. Specifically, in one such embodiment, suture ring 1500 tapers (or flares) away at the lower portion 1520b to create a flattened collar or skirt that can be applied against and sutured to the patent's prepared annulus. However, the shape of suture ring 1500 may be different for different applications (e.g., mitral valve replacement versus aortic valve replacement). Accordingly, it should be appreciated that suture ring 1500 may adopt any desired shape or cross-section profile.

In the embodiment of FIG. 4, the frame 1300 (shown in more detail in FIG. 5) is cylindrical in shape, having an axis X2. The frame 1300 includes an interior face 1320 and an exterior face 1330, as well as an upper portion 1340*a* and a lower portion 1340*b*. In various embodiments, the valve frame 1300 includes one or more commissure posts 1350, such as commissure posts 1350*a*, 1350*b*, and 1350*c*. The commissure posts 1350 extend from the lower portion 1340*b* of the frame 1300 and facilitate the proper configuration, operation, and orientation of the tissue leaflets (not shown). In certain embodiments, the commissure posts 1350 include one or more apertures 1360, which help facilitate the coupling of the tissue leaflets to the commissure posts 1350. Though not illustrated FIGS. 4 and 5, it should be appreciated that, in certain embodiments, apertures 1360 may extend along a bottom periphery of the lower portion 1340*b*.

In various embodiments, valve retention ring 1400 and suture ring 1500 (FIG. 4) are coupled together and comprise a single unit. That is, in certain embodiments, valve retention ring 1400 and suture ring 1500 are fastened together prior to being implanted into a patient. In one such embodiment, suture ring 1500 and valve retention ring 1400 are stitched together. In yet another embodiment, some other suitable method (e.g., rivets, clips, or pins) is employed to couple valve retention ring 1400 and suture ring 1500 to form abutment ring 1200. For example, in one embodiment, stitches are passed through the suture permeable fabric 1510 of the upper portion 1520*a* of suture ring 1500 and through upper apertures 1440*a* of the upper portion 1430*a* of valve retention ring 1400. In some embodiments, stitches are additionally (or alternatively) passed through the suture permeable fabric 1510 of the lower portion 1520*b* of suture ring 1500 and through the lower apertures 1440*b* of the lower portion 1430*b* of valve retention ring 1400. It should be appreciated, however, that the valve retention ring 1400 and the suture ring 1500 may be fastened together via any suitable fastening means or configuration.

Figure 5:
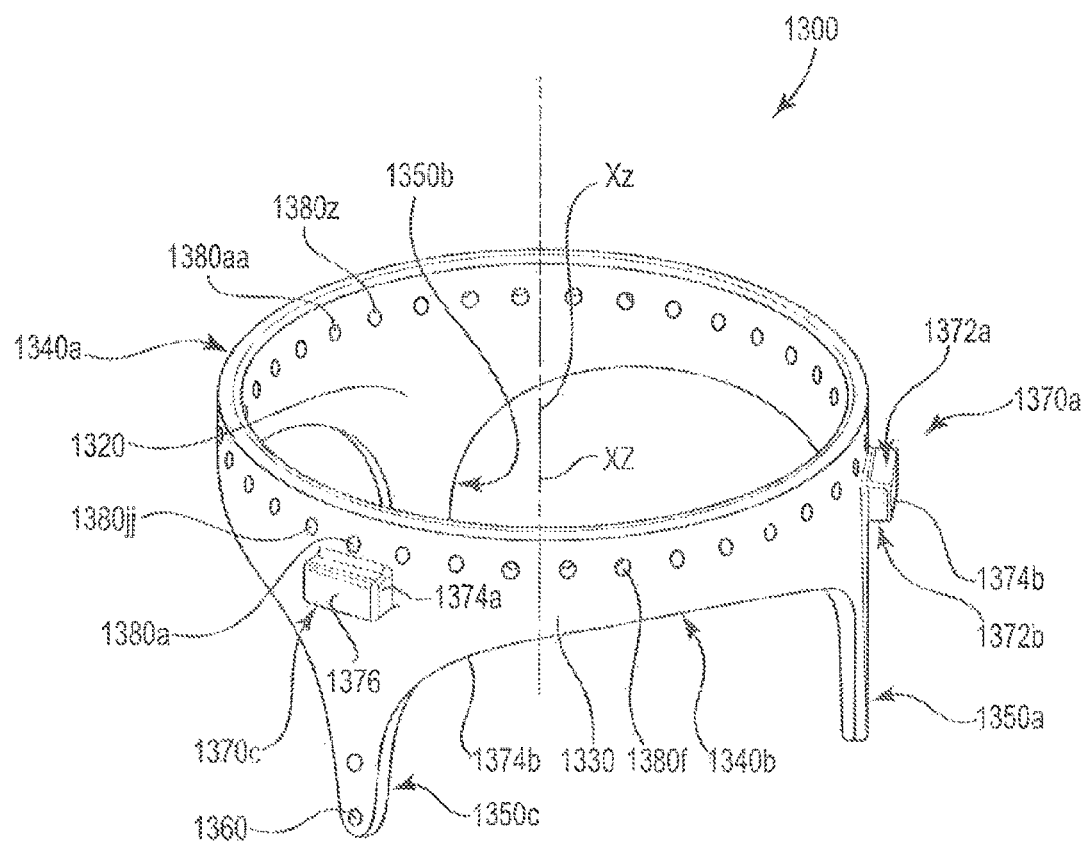
FIG. 5 is a perspective view illustrating a valve frame of the embodiment of FIG. 4, according to some embodiments described in the disclosure.

In various embodiments, valve frame 1300 (FIGS. 4 and 5) is configured to be removably coupled to the abutment ring 1200. That is, after abutment ring 1200 is implanted, valve frame 1300 may be subsequently coupled to and decoupled from abutment ring 1200. In one such embodiment, valve frame 1300 includes one or more locking features 1370, such as locking features 1370*a*, 1370*b* (not visible in FIG. 4), and 1370*c*. Locking features 1370 are protrusions or bosses extending from the exterior face 1330 of the frame 1300 and traversing a portion of less than an entirety of the circumference of the exterior surface 1330 of valve frame 1300. As shown in FIG. 5, locking features 1370 include an upper surface 1372*a*, a lower surface 1372*b*, a first side surface 1374*a* (shown with reference to locking feature 1370*c*), as well as a second side surface 1374*b* (shown with reference to locking feature 1370*a*), and an exterior surface 1376 (shown with reference to locking feature 1370*c*). While the locking features 1370 illustrated in FIG. 4 are rectangular in shape, it should be appreciated that the locking features 1370 may be of any suitable size or shape.

In various embodiments, abutment ring 1200 is configured to receive valve frame 1300. In one embodiment, the diameter of the interior face 1410 of valve retention ring 1400 is sized such that valve frame 1300 may be received within valve retention ring 1400. In some embodiments, in addition to being configured to receive valve frame 1300, abutment ring 1200 is configured to retain valve frame 1300. Specifically, valve retention ring 1200 includes a locking system, which operates together with locking features 1370 of valve frame 1300 to provide a means for removably coupling valve frame 1300 to abutment ring 1200.

In one embodiment, the locking system of valve retention ring 1400 includes one or more locking feature cavities 1450 (such as locking feature cavities 1450*a*, 1450*b*, and 1450*c*) within which the locking features 1370 of valve frame 1300 may be received. In certain embodiments the locking feature cavities 1450 include locking feature relief surfaces 1460, 1462*a* and 1462*b* and locking feature channels 1470.

As illustrated in FIG. 5, a plurality of apertures 1380 is positioned along the circumferential perimeter of the upper portion 1340*a* of the frame 1300. In the embodiment illustrated in FIG. 5, each of the apertures 1380 extends from the interior face 1320 to the exterior face 1330 such that each aperture's axis extends generally perpendicular relative to axis X2 of valve frame 1300. In certain embodiments, the apertures 1380 help facilitate the coupling of the tissue leaflets to the frame 1300. However, the coupling of the tissue leaflets to the frame 1300 may be done in any suitable manner as would be appreciated by one of ordinary skill in the art.

Figure 6:
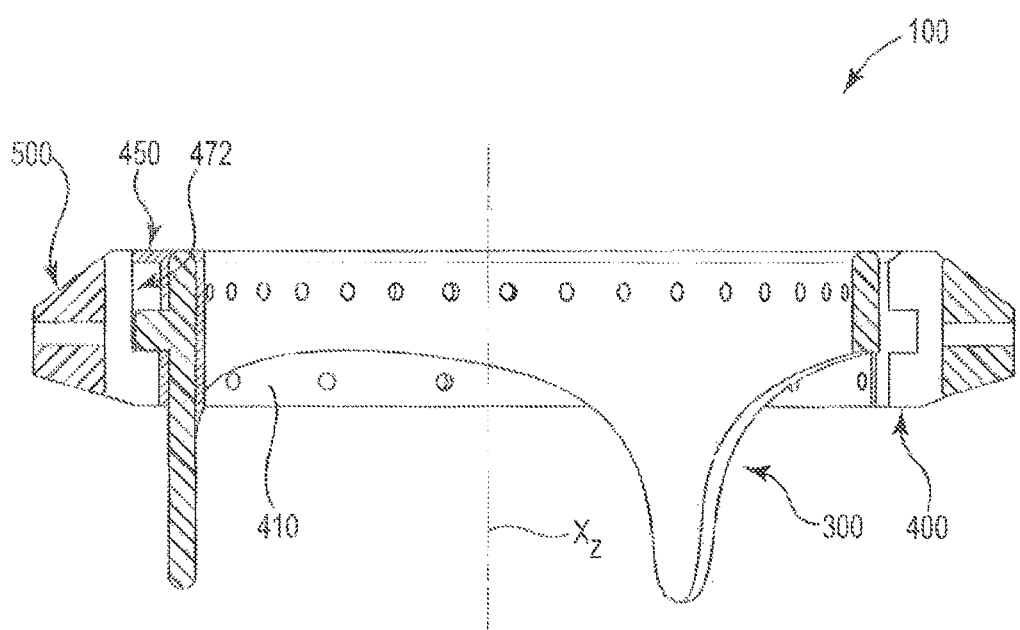
FIG. 6 is a cross-sectional side view of the bioprosthetic heart valve system of FIG. 4, according to some embodiments described in the disclosure.

As shown for example in FIG. 4, in some embodiments, the locking feature relief surfaces 1460 and locking feature channels 1470 of each locking feature cavity 1450 are recessed into interior surface 1410 of valve retention ring 1400. In one embodiment, each locking feature cavity 1450 includes an interior face 1460, which is curved about the axis X1 and is offset therefrom by a radial distance that exceeds the radial distance by which interior surface 1410 is offset from axis X1 (see also FIG. 6).

In one embodiment, each locking feature channel 1470 extends in a circumferential direction, generally perpendicular to and about axis X1. In various embodiments, the locking feature channels 1470 each includes a first end 1474*a* and a second end 1474*b*, and an upper face 1476*a* and a lower face 1476*b*. Likewise, each locking feature cavity 1450 include recess surfaces 1460, as well as a first side face 1462*a* and a second side face 1462*b*, wherein the first and second side faces 1462*a* and 1462*b* generally extend axially along axis X1 and are generally perpendicular to upper and lower faces 1476*a* and 1476*b* of locking feature channels 1470. As illustrated in FIG. 4, the second ends 1474*b* of locking feature channels 1470 facilitate a smooth transition between the side faces 1462*a*, 1462*b* of the locking feature cavity and the upper and lower faces 1476*a*, 1476*b* of the locking feature channels 1470.

In some embodiments, locking feature cavities 1450 are also open at a top portion 1478 such that the locking features 1370 can be received within locking feature cavities 1450. In one such embodiment, the first and second side faces (1462*a* and 1462*b*) of locking cavities 1450 are parallel (or are substantially parallel) to one another. In another such embodiment, the first and second side faces (1462*a* and 1462*b*) of locking feature cavities 1450 taper away from one another slightly from bottom to top. It should be appreciated that such a taper provides ease when aligning the coking features 1370 of the valve frame 1300 with the locking feature cavities 1450 of the valve retention ring 1400.

In various embodiments, locking feature cavities 1450 of valve retention ring 1400 are configured to receive locking features 1370 of the valve frame 1300. Specifically, in these embodiments, as valve frame 1300 is inserted into valve retention abutment ring 1200, locking features 1370 of the valve frame 1300 are aligned with locking feature cavities 1450 of valve retention ring 400. Such an alignment requires each first side face 1374a of each locking feature 1370 to be aligned with each first side face 1462a of each locking feature cavity 1450, and each second side face 1374b of each locking feature 1370 to be aligned with each second side face 1462b of each locking feature cavity 1450. It should be noted that the distance between the first and second side faces (1374a and 1374b) of locking features 1370 is slightly less than the distance between the first and second side faces (1462a and 1462b) of each locking feature cavity 1450. Valve frame 1300 is inserted into abutment ring 1200 until it reaches a disengaged position.

Figure 7A:
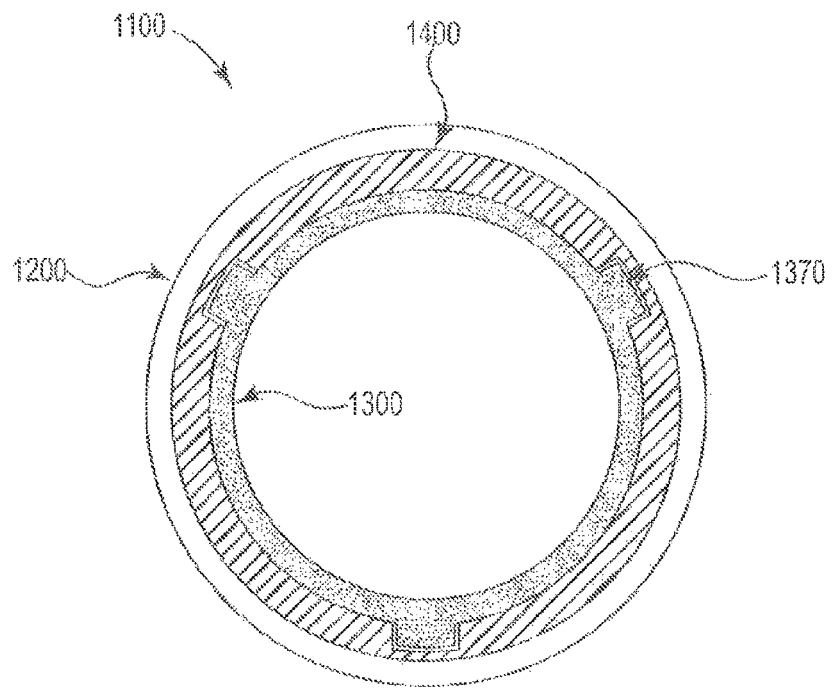
FIGS. 7A and 7B are top-views of the bioprosthetic heart valve system of FIG. 4, in disengaged and engaged configurations, respectively, according to some embodiments described in the disclosure.

As shown in FIG. 7A, valve frame 1300 is illustrated, from a top view, in a disengaged, unlocked position. In the disengaged position, valve frame 1300 is fully inserted within abutment ring 1200 such that the lower faces 1372b (see also FIGS. 4-5) of locking features 1370 come into contact with (or are otherwise within a sufficient proximity to) the lower faces 1476b of the locking feature channels 1470. Despite being fully inserted within abutment ring 1200 while in the disengaged position, valve frame 1300 is not locked within (or otherwise retained by) abutment ring 1200 and can be removed (i.e., axially translated along axis X1) free from any manipulation or contact with abutment ring 1200.

In one embodiment, the valve frame 1300 can be transitioned from the disengaged position to one of a plurality of engaged (or axially constrained) positions. Transitioning the valve frame 1300 from the disengaged position to an engaged position is accomplished via rotation of the valve frame 1300 a sufficient degree about axis X1 relative to abutment ring 1200. In one embodiment, when transitioning the valve frame 300 from the disengaged position to an engaged position (or vice versa) the abutment ring 1200 (including the valve retention ring 1400) remains secured to the patient's annulus and does not rotate. However, valve frame 1300 remains free to rotate to an engaged position relative to the abutment ring 1200. In one embodiment, when valve frame 1300 is rotated from the disengaged position to an engaged position, valve frame 1300 is constrained from axial movement by engagement of the locking features 1370 within locking feature channels 1470.

In one embodiment, the ease with which the valve frame 1300 may be rotated depends at least in part, on the amount of clearance between the upper and lower faces (1372a and 1372b) of locking features 1370 and the upper and lower faces (1476a and 1476b) of the locking feature channels 1470. That is, the force (or torque) required to rotate valve frame 1300 relative to abutment ring 1200 depends at least in part, on a level of clearance between valve frame 1300 and valve retention ring 1400.

In certain embodiments, there is no clearance or even negative clearance between valve frame 1300 and valve retention ring 1400. That is, the distance between the upper and lower faces (1372a and 1372b) of locking features 1370 is greater than or equal to the distance between the upper and lower faces (1476a and 1476b) of locking feature channels 1470. Such a lack of clearance creates an interference fit in which frictional resistance inhibits (but does not prohibit) rotational movement of valve frame 1300. It should be appreciated that the force (or torque) required to rotate the valve frame 1300 in such embodiments will depend on both the material properties of the valve frame 1300 and the valve retention ring 1400, and the difference between the height of the locking features 1370 (i.e., the distance between upper and lower surfaces 1372a and 1372b) and the height of locking feature channels 1470 (i.e., the distance between upper and lower faces 1476a and 1476b).

In various embodiments where an interference fit is utilized to inhibit (but not prohibit) relative rotational movement between valve frame 1300 and valve retention ring 1400, frame 1300 and ring 1400 are sized (and material properties are selected) such that frame 1300 can be rotated during the implantation procedure without damaging either component, the patient's heart valve annulus, or any of the surrounding tissue. Likewise, the relative sizing and material properties are selected such that the level of force (or torque) required to cause valve frame 1300 to rotate exceeds any potential forces that might act upon the valve assembly 1100 during natural heart function. Such a configuration ensures that valve frame 1300 cannot rotate during normal heart function. In one embodiment, the materials and dimensional tolerances between the valve frame and the valve retention ring are selected such that rotation of the heart valve (and specifically the heart valve frame 1300) relative to the valve retention ring 1400 will not occur unless a torque exceeding a first rotational threshold is applied to the heart valve or heart valve frame.

In one embodiment, as valve frame 1300 is rotated relative to abutment ring 1200, locking features 1370 pass into locking feature channels 1470. In one embodiment, once a sufficient portion of locking features 1370 have passed into locking feature channels 1470, valve frame 1300 is engaged with abutment ring 1200. That is, valve frame 1300 is positioned in an engaged position and cannot translate axially along axis X1.

Figure 7B:
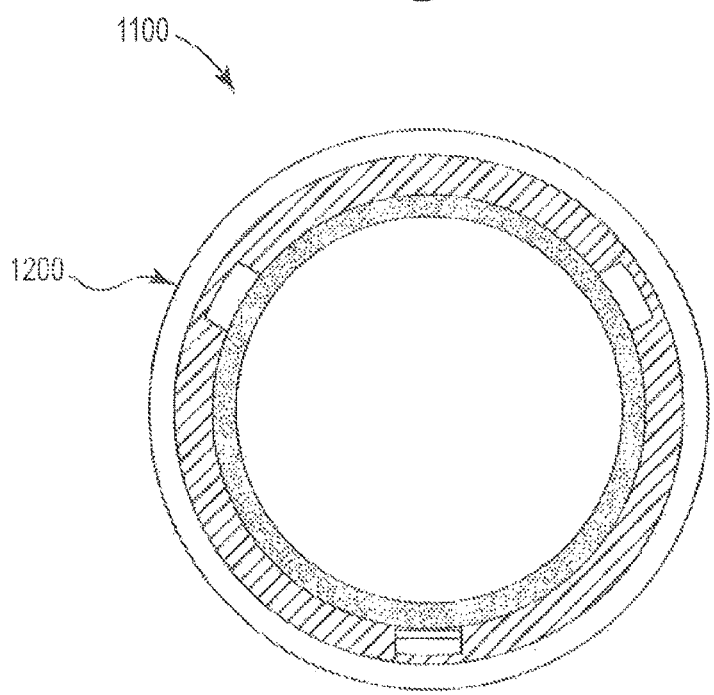

For example, as shown in FIG. 7B, valve frame 1300 is illustrated, from a top view, in an engaged, axially constrained position (see also FIG. 4). With locking features 1370 received within locking feature channels 1470, locking features 1370 of valve frame 1300 are axially constrained from above by upper and lower faces 1476a and 1476b, respectively, of locking feature channel 1470. Accordingly, while in the engaged position, upper and lower faces 1476a and 1476b of locking feature channels 1470 operate to prohibit axial translation (or axial movement) of valve frame 1300 relative to abutment ring 1200 and valve retention ring 1400 along axis X1.

Further, as discussed in greater detail below, in some embodiments the construction of locking feature channels 1470 permit valve frame 1300 to be positioned in any of a plurality of different engaged positions from the disengaged position, shown in FIG. 7a, in which locking features 1370 are seated within locking feature cavities 1450, but with no angular rotation therefrom. That is, after being rotated from the disengaged position to a first engaged position in which the locking features 1370 are displaced by a first angle relative to abutment ring 1200 and valve retention ring 1400, valve frame 1300 remains free to be rotated to a second, different engaged position at a different angular displacement from abutment ring 1200 and valve retention ring 1400. Such a configuration provides flexibility in allowing the surgeon to set the orientation of the valve frame relative to the left ventricular outflow tract (LVOT) as discussed further below.

In the illustrated embodiment of FIG. 4, each locking feature channel 1470 spans an arc of about eighty (80) degrees. Accordingly, the locking features 1370 may be rotated (by rotating valve frame 1300) within the locking feature channels 1470 to any engaged position between greater than zero (0) degrees and less than eighty (80)

degrees relative to the locking feature cavities 1450. For example, valve frame 1300 may be rotated to a first engaged position by being rotated by an angle of sixty (60) degrees from the disengaged position of FIG. 7A. Similarly, in this example, valve frame 1300 may be rotated to a second, different engaged position by being rotated by an additional twenty (20) degrees. Thus, it should be appreciated that, in various embodiments, valve frame 1300 may be rotated to any number of engaged positions, provided that the locking features 1370 are constrained by the upper and lower surfaces 1476a and 1476b of locking feature channels 1470.

It should be appreciated that the transition from the disengaged position to an engaged position (or vice versa) does not first require manipulation of the abutment ring 1200 or manipulation of the valve retention ring 1400. That is, while positioned in an engaged position, rotation of valve frame 1300 does not first require manipulation of the abutment ring 1200 or manipulation of the valve retention ring 1400. Instead, valve frame 1300 may be transitioned from the disengaged position to an engaged position (and vice versa) free from any such manipulation without risking damage to the patient's heart annulus or surrounding tissue. Such a configuration provides for rapid and efficient implantation and removal procedures, and a corresponding decreased risk to the patient.

In certain alternative embodiments, after valve frame 1300 has been fully inserted and rotated to the desired engagement position, valve frame 1300 and abutment ring 1200 may be fastened together to prevent further rotational movement relative to one another. For example, one or more sutures may be employed to couple together valve frame 300 and abutment ring 1200.

Wile the embodiment illustrated in FIG. 4 includes a plurality of separate and district locking feature channels 1470, it should be appreciated that certain alternative embodiments may employ one continuous locking feature channel, in contrast to the three separate channels shown in FIG. 4. In these alternative embodiments, valve retention ring 1400 includes a single, continuous locking feature channel and one or more locking feature cavities 1450. Specifically, each of the locking feature cavities 1450 is coupled to the single continuous locking feature channel such that as valve frame 1300 is inserted into valve retention ring 1400, locking features 1370 are received by the locking feature cavities 1450. Once valve frame 1300 is fully inserted (e.g., in the disengaged, un-rotated position of FIG. 7A), the first and second side surfaces 1374a and 1374b of the locking features 1370 are aligned with the first and second side surfaces (similar to the left and right side surfaces 1462a and 1462b of the locking feature cavities 1450 of FIG. 4), and the lower surface 1372b of the locking feature 1370 is in contact with (or is sufficiently proximate to) the lower surface of the single continuous locking feature channel (similar to the lower surface 1476b of the locking feature channels 1470 of FIG. 4). Accordingly, valve frame 1300 is permitted to rotate in either direction (clockwise or counter clockwise) such that locking features 1370 enter and are received by the single continuous locking feature channel (e.g., engagement). Thereafter, rotation of the valve frame 1300 operates in accordance with the embodiments discussed above. This type of alternative configuration provides additional degrees of freedom to the valve frame 1300.

The locking system discussed above can alternatively consist of a snap-in feature which is activated through the pushing of the valve frame inside the abutment ring (already sutured to the valvular rim or annulus). Put differently, while certain embodiments include locking feature channels 1470, certain alternative embodiments are devoid of locking feature cavities 1450. In one such embodiment, the valve retention ring includes a single continuous locking feature channel (or alternatively a plurality of locking feature channels similar those illustrated in FIG. 4), which is configured to receive the looking features 1370 of valve frame 1300.

In these embodiments, the one or more locking features 1370 of valve frame 1300 may comprise resilient members that are configured to deflect (or otherwise temporarily deform) as the valve frame is inserted into the valve retention ring, without the presence of locking feature cavities 1450. This deflection permits the valve frame to fit within the interior surface of the valve retention ring 1400. Specifically, the locking features 1370 deflect as valve frame 1300 is inserted into the valve retention ring 1400, and remain deflected due to interference with an interior surface 1410 of the ring 1400. In one embodiment, the locking features remain deflected until the valve frame 1300 is in a position where the locking features no longer interfere with the interior surface of the valve retention ring 1400.

In one such embodiment, the position is one in which the valve frame is positioned within the valve retention ring such that the locking features are aligned with a locking feature channel and are thus free to return to their original undeflected state. As the locking features return to their undeflected state, they enter into and are received by the locking feature channel. Thereafter, rotation of the valve frame 1300 operates in accordance with the embodiments discussed above.

Additionally, while the figures illustrate the looking feature cavities 1450 being positioned at an end (e.g., 1474b, as shown in FIG. 4) of the locking feature channels 1470, in certain alternative embodiments, the locking feature cavities 1450 are positioned between each of the ends 1474a and 1474b of the locking feature channel 1470. Accordingly, once positioned in the disengaged position valve frame 1300 may be rotated in either direction (e.g., clockwise or counter clockwise; relative to the valve retention ring 1400. Thereafter, rotation of the valve frame 1300 operates in accordance with the embodiments discussed above.

Moreover, while the illustrations accompanying the embodiments described herein involve three (3) locking features 1370, three (3) locking feature cavities 1450, and three (3) locking feature channels 1470, it should be appreciated that any suitable number of locking features 1370, locking feature cavities 1450, and locking feature channels 1470 may be employed without departing from the spirit and scope of the envisioned embodiments.

In another alternative embodiment a third element is interposed between the valve retention ring end the valve frame. In this embodiment, an inner surface of the third element is configured to interface with the outer surface of the valve frame (for example, fixed with sutures or forced on the valve frame), while an outer surface of the third element is configured to interface with the locking feature cavity 1450 of the valve retention ring. In one embodiment, the third element is configured to rotate (like a bearing) with respect to the valve retention ring, or the valve frame, or both.

In one embodiment, this third bearing element can be screwed onto the exterior surface 330 of the valve frame 300 (or alternatively screwed into the interior surface 410 of the valve retention ring).

In another alternative embodiment the valve retention ring 1400 includes a sealing member configured to fill any gap that might otherwise exist between the valve retention ring and the valve frame after the valve frame is positioned in an engaged position. In one such embodiment, the sealing member is at least a portion of the suture ring, in another such embodiment, the sealing member is a coating or filling applied to the interior surface 1410 of the valve retention ring prior to implantation. In yet another such embodiment, the sealing member is a coating or filling applied after implantation. In one embodiment, the sealing member is made of acetalic resin, silicone, rubber, or other biocompatible plastic material and/or stainless steel, or titanium, or other biocompatible metallic material.

Figure 9:
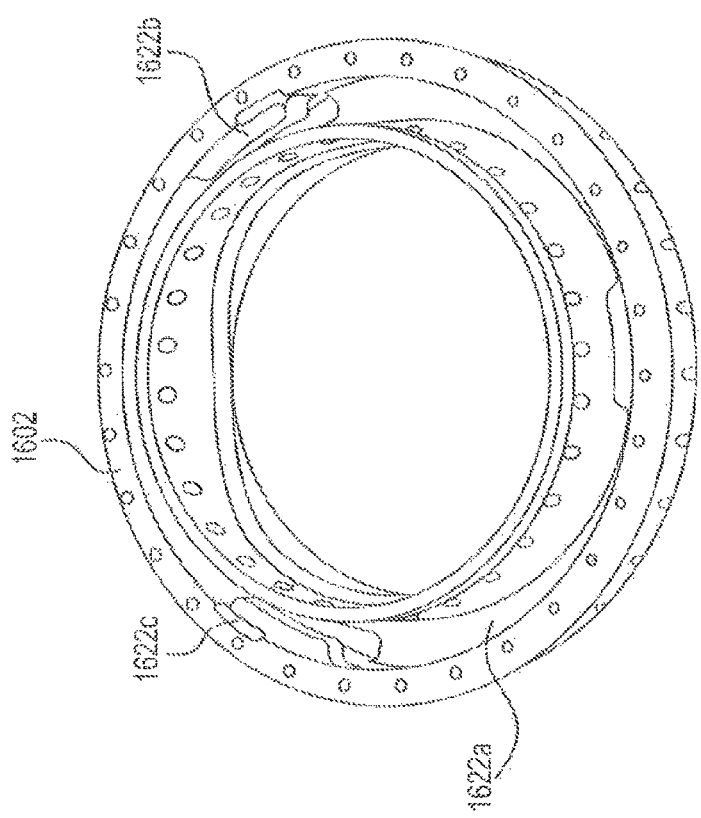
FIG. 9 is a perspective view of a bottom side of a frame of the bioprosthetic heart valve system of FIG. 8, according to some embodiments described in the disclosure.

FIG. 8 illustrates a partially exploded view of a bioprosthetic heart valve system 1600 including a valve frame 1602 and an abutment ring 1604. FIG. 9 illustrates a bottom view of the valve frame 1602. FIG. 10 illustrates a section side view of the valve frame 1602 and abutment ring 1604.

Together, valve frame 1602, abutment ring 1604, and a plurality of tissue leaflets (not shown) generally make up the structure of the implantable prosthetic heart valve assembly 1600. The abutment ring 1604 includes a valve retention ring 1608 and a suture ring 1610. In one embodiment, valve retention ring 1608 is ring shaped (or cylindrically shaped) with a ho low interior. For example, as shown in FIG. 8, valve retention ring 1608 is in the shape of a ring and has a central axis X1. Valve retention ring 1608 has an interior face 1612 and an exterior face 1614. In some embodiments, as discussed above, valve retention ring 1608 includes one or more features, like apertures 1616, which facilitate fastening valve retention ring 1608 to suture ring 1610. As illustrated in FIG. 8, apertures 1616 are positioned along a circumferential perimeter of valve retention ring 1608.

In one embodiment, valve retention ring 1808 includes a first ledge 1618 extending from the exterior face 1614 towards the central axis X1. The first ledge 1618 includes a plurality of openings or cutaway portions 1620*a-c* about the central axis X1. The plurality of openings 1620*a-c* have locations and shapes in order to allow a plurality of corresponding locking features 1622*a-c* on the valve frame 1602 (FIG. 9) to pass through the plurality of openings 1620*a-c* to form a seating structure for frame 1602 on valve retention ring 1608. The valve frame 1602 is configured to be assembled to the valve retention ring 1608 by inserting the locking features 1622*a-c* of the valve frame 1602 through the plurality of corresponding openings 1620*a-c* of the valve retention ring 1608. The valve frame 1602 is further configured to be retained to the valve retention ring 1608 by rotating the valve frame 1602 to cause the locking features 1622*a-c* to travel along channel 1626, which is positioned between the first ledge 1618 and a second ledge 1624 (FIG. 10). In certain embodiments, the valve retention ring 1608 includes the first ledge 1618 but not the second ledge 1624. Valve frame 1602 may be rotated until each locking feature 1622*a-c* or at least a portion of each locking feature, extends into and engages with a recess formed in the first ledge 1616, for example, such as the recess 438 shown in FIG. 3A. For example, each locking feature 1622*a-c* can includes a boss or protrusion that is shaped to engage with the recess such that the valve frame 1602 maintains its position with respect to the valve retention ring 1608.

FIG. 11 illustrates a partially exploded view of portions of a bioprosthetic heart valve system 1700 including a valve frame 1702 that is configured to be coupled to a valve retention ring 1704. Together, valve frame 1702, valve retention ring 1704, and a plurality of tissue leaflets (not shown) generally make up the structure of the implantable prosthetic heart valve assembly 1700. The valve retention ring 1704 is ring shaped (or cylindrically shaped) with a hollow interior and has a central axis X1. Valve retention ring 1704 has an interior face 1708 and an exterior face 1710. In some embodiments, as discussed above, valve retention ring 1704 includes one or more features, like apertures 1712, which provide for fastening valve retention ring 1704 to a suture ring (not shown). As illustrated in FIG. 11, apertures 1712 are positioned along a circumferential perimeter of valve retention ring 1704.

In one embodiment, valve retention ring 1704 includes one or more locking features 1714 on the interior face 1708. The locking features 1714 are arranged and shaped to couple to channels 1716 positioned on an exterior face of the valve frame 1702. The valve frame 1702 includes openings or cutaway portions 1718 that have locations and shapes in order to allow corresponding locking features 1714 on valve retention ring 1704 to pass through. The valve frame 1702 is configured to be assembled to the valve retention ring 1704 by inserting the locking features 1714 of the valve retention ring 1704 through the plurality of corresponding cutaway portions 1718 of the valve frame 1702. The valve frame 1702 is further configured to be retained to the valve retention ring 1704 by rotating the valve frame 1702 relative to the valve retention ring 1704 to cause the locking features 1714 of ring 1704 to travel along channels 1716 of frame 1702. In one embodiment, valve frame 1702 may be rotated until each locking feature 1714 extends into channel 1716 and engages with several half-spherical recesses disposed along the channel 1716. The locking features 1714 are snap-fit features with a half-spherical protrusion which fit with the half-spherical recess of the channel 1716.

Turning now to FIGS. 12A to 12D, a surgical implantation procedure of a multi-component heart valve prosthesis in accordance with an embodiment of the present disclosure is illustrated. As discussed above, prior to implantation, the patient's annulus is prepared. In some instances, this may involve little or no alteration of the annulus, while in other cases surgical removal of one or more portions of the damaged or diseased natural valve structure, such as removal of the valve leaflets and/or resection of a portion of the annulus. Once the annulus has been prepared, a surgeon will secure one or more "pilot" sutures 2000 to the patient's annulus (or the tissue surrounding the patient's annulus), which will be later used to locate and secure the sewing ring abutment 1200 to the patient's annulus. In some embodiments, after the one or more pilot sutures are secured, each of the one or more pilot sutures 2000 are delivered through the suture permeable fabric of the suture ring such that the abutment ring 1200 may be "parachuted" along the sutures and properly positioned with respect to the patient's annulus.

Figures 12A, 12B:
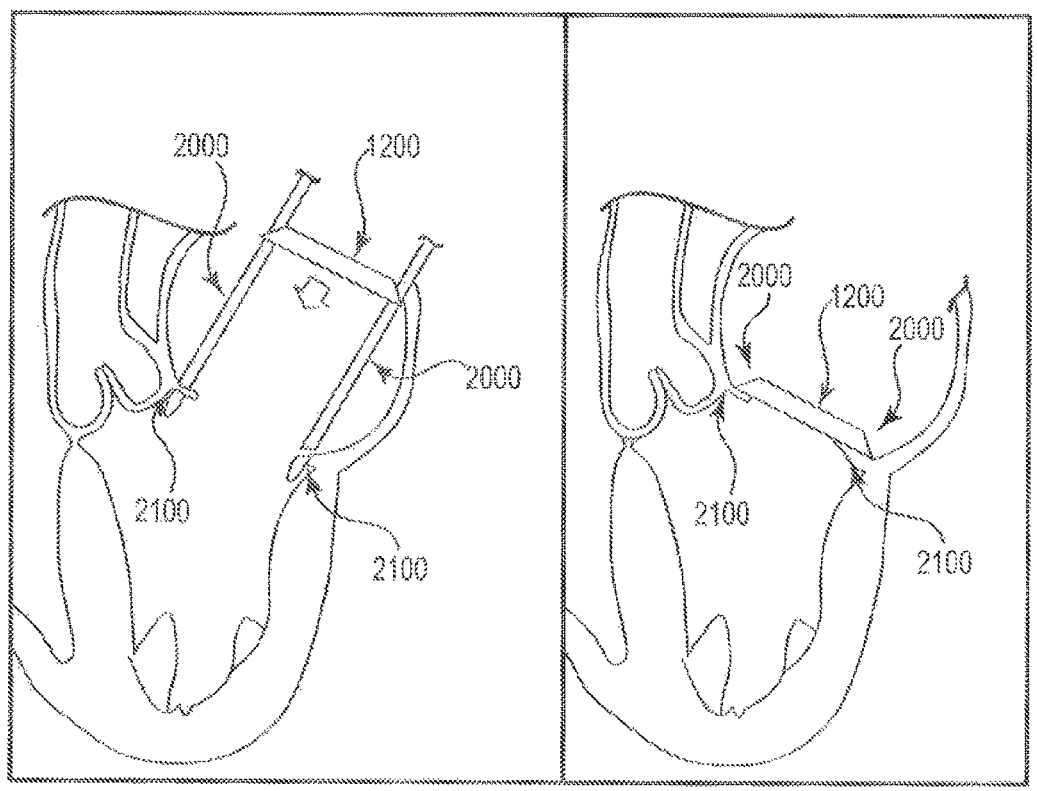
FIGS. 12A to 12D illustrate an implantation procedure of the bioprosthetic heart valve system, according to some embodiments described the disclosure.

For example, as illustrated by the arrow in FIG. 12A, in one embodiment, abutment ring 1200 is parachuted along sutures 2000 toward the patient's annulus 2100. At this point in the implantation procedure, the valve frame 1300 is decoupled from the abutment ring 1200. That is, in this embodiment, abutment ring 1200, without valve frame 1300, is parachuted along the sutures 2000 toward the patient's valve rim 2100. Thereafter, abutment ring 1200 is secured to the patient's annulus 2100 by tying-off the one or more pilot sutures 2000. For example, as illustrated in FIG. 12B, after abutment ring 1200 is properly located with respect to the annulus 2100, sutures 2000 are tied off such that abutment ring 1200 is fully secured to the annulus. With abutment ring 1200 fully secured to the patients valve rim 2100 (i.e., pilot sutures 2000 are tied off), abutment ring 1200 is prohibited from rotating or translating relative to the patient's annulus.

Moreover, at this point in the procedure, because valve frame 1300 is decoupled from abutment ring 1200 (i.e., valve 1300 is not yet implanted), the ventricular side of the patient's heart remains visible through the abutment ring 1200. Accordingly, the surgeon can visually confirm from both the atrial and ventricular sides of the patient's heart that abutment ring 1200 has been properly positioned, that the pilot sutures have been properly secured, and that no obstructions or procedure-related anomalies exist.

Figures 12C, 12D:
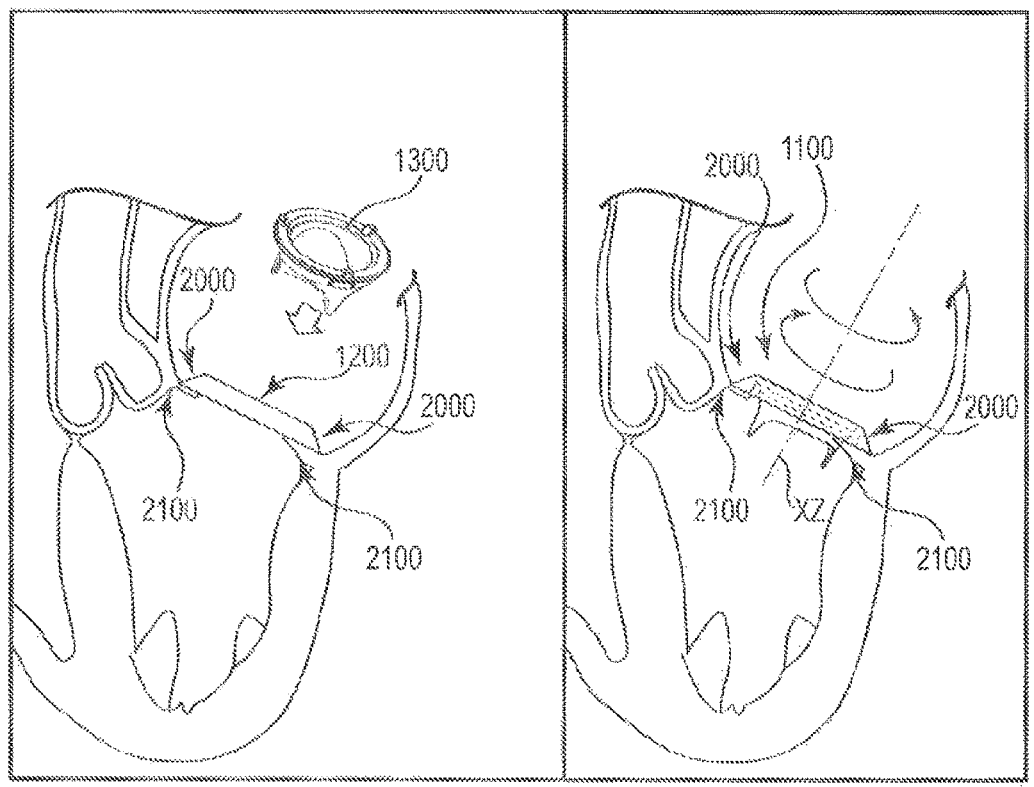

Turning now to FIG. 12C, in one embodiment, after abutment ring 1200 has been secured to the patients annulus 2100, and after each of the pilot sutures 2000 (and any additional sutures utilized to secure abutment ring 1200) have been tied-off, valve 1300 is inserted into abutment ring 1200. The illustrated example of FIG. 12C depicts valve 1300 traveling toward abutment ring 1200 from the atrial side of the patients heart. As discussed above, valve 1300 is aligned with and inserted into abutment ring 1200. It should be appreciated that the ability to secure the pilot sutures 2000 (and any additional sutures utilized to secure abutment ring 1200) prior to inserting valve 1300 into abutment ring 1200 provides for an implantation procedure that completely avoids the suture looping problem (discussed above) prevalent in the poor art. Such an implantation procedure also provides increased visibility of the ventricular side of the heart during the suturing phase of the procedure.

As shown in FIG. 12D, in various embodiments, after valve 1300 is inserted into abutment ring 1200, valve 1300 may be rotated to any of a plurality of different radial positions relative to the abutment ring (as discussed in greater detail above). For example, after insertion, valve 1300 can be rotated from a disengaged position to a first engaged position by rotating valve 1300 in a first direction (clockwise or counter clockwise). Moreover, after valve 1300 has been rotated to the first engaged position, it remains free to be rotated from the first engaged position to a second, different engaged position by rotating valve 1300 in either the first direction or a different direction (counter clockwise or clockwise). That is, even after valve 1300 has been positioned by the surgeon, it remains free to be repositioned to another engaged position without first manipulating the abutment ring 1200, the suture ring 1500, or the valve retention ring 1400, and without risk of damaging the patient's annulus or surrounding tissue.

This freedom to manipulate the rotational position of valve 1300 provides surgeons the ability to fine-tune the prosthetic heart valve assembly 1100 efficiently and effectively. This permits surgeons to manipulate the rotational positioning of valve 1300 such that the commissure posts 1350 are properly positioned relative to the natural blood flow paths of the heart. Specifically, surgeons can rotate valve 1300 such that the commissure posts 1350 do not interfere with the left ventricular outflow tract (LVOT), thereby avoiding LVOT obstructions.

Finally, after valve frame 1300 has been positioned in a final engaged position, valve frame 1300 remains free to the repositioned to the disengaged position (discussed above), and thereafter removed, without further manipulating the abutment ring 1200, the suture ring 1500, or the valve retention ring 1400, and without risk of imaging the patient's annulus or surrounding tissue. Accordingly, the novel construction and operation of the prosthetic heart valve assembly 1100 of the above discussed embodiments provides for efficient and accurate implantation, removal, and replacement of a heart valve prosthesis without risk of damaging vital components of the prosthesis or surrounding tissue, such as the annulus.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with ail equivalents thereof.

We claim:

1. A multiple component heart valve prosthesis for implantation at a heart valve annulus location of a patient's heart, the heart valve prosthesis comprising:
    an abutment ring configured for attachment at the heart valve annulus location and including a locking system comprising at least one channel positioned on an exterior surface of the abutment ring, a ledge extending from the exterior surface of the abutment ring to form the at least one channel, and a spring-like structure comprising a clip; and
    a removable bioprosthetic heart valve comprising a valve frame and at least one locking feature, the at least one locking feature configured to be received by the locking system,
    wherein the bioprosthetic heart valve is configured to be rotated relative to the abutment ring such that the at least one locking feature transitions from a disengaged position to a first engaged position,
    wherein, in the disengaged position, the bioprosthetic heart valve may be removed from the abutment ring, and
    wherein, in the engaged position, the bioprosthetic heart valve is restrained from axial movement relative to the abutment ring.

2. The heart valve prosthesis of claim 1, wherein the ledge comprises at least one opening.

3. The heart valve prosthesis of claim 2, wherein the at least one channel is configured to accept the at least one locking feature of the removable bioprosthetic heart valve via the at least one opening, such that the removable bioprosthetic heart valve is rotatable relative to the abutment ring within the at least one channel.

4. The heart valve prosthesis of claim 2, wherein the locking system comprises a recess disposed on the ledge of the abutment ring.

5. The heart valve prosthesis of claim 4, wherein the locking feature comprises a boss configured to engage with the recess of the locking system.

6. The heart valve prosthesis of claim 1, wherein the abutment ring comprises a valve retention ring comprising the locking system, and a suture ring configured to be coupled to the valve retention ring, the valve retention ring comprising a plurality of apertures configured to facilitate fastening of the suture ring to the valve retention ring.

7. The heart valve prosthesis of claim 1, wherein when positioned in the first engaged position, the removable bioprosthetic heart valve remains free to be rotated relative to the abutment ring from the first engaged position to a second engaged position.

8. The heart valve prosthesis of claim 7, wherein a height of the at least one channel and a height of the at least one locking feature are selected to provide an interference fit configured to require a torque exceeding a first rotational threshold to cause the removable bioprosthetic heart valve to be rotated relative to the abutment ring.

9. The heart valve prosthesis of claim 1, wherein the locking system of the abutment ring includes a plurality of channels.

10. The heart valve prosthesis of claim 9, wherein the removable bioprosthetic heart valve includes a plurality of locking features.

11. The heart valve prosthesis of claim 1, further comprising a locking feature configured to secure the removable bioprosthetic heart valve within the abutment ring once positioned in a desired position such that the removable bioprosthetic heart valve is prevented from being further rotated relative to the abutment ring.

12. The heart valve prosthesis of claim 1, wherein the abutment ring is configured to be attached to a patient's mitral valve rim.

13. A method of implanting a multiple component heart valve prosthesis, the method comprising:
securing an abutment ring to a heart valve annulus of a patient's heart, the abutment ring comprising a locking system including at least one channel positioned on an exterior surface of the abutment ring, a ledge extending from the exterior surface of the abutment ring to form the at least one channel, and a spring-like structure comprising a clip;
inserting a removable bioprosthetic heart valve into the abutment ring such that at least one locking feature of the bioprosthetic heart valve is received by the locking system in a disengaged position; and
rotating the removable bioprosthetic heart valve relative to the abutment ring such that the at least one locking feature rotates within the at least one channel from the disengaged position to an engaged position where the removable bioprosthetic heart valve is prohibited from axial movement relative to the abutment ring.

14. The method of claim 13, wherein the abutment ring comprises a valve retention ring and a suture ring configured to be coupled to the valve retention ring, the valve retention ring comprising the locking system, and wherein securing the abutment ring to the heart valve annulus comprises securing the suture ring to the heart valve annulus.

15. The method of claim 13, wherein, in the engaged position, the removable bioprosthetic heart valve remains free to be rotated relative to the abutment ring from the engaged position to a second engaged position.

16. The method of claim 13, wherein rotating the removable bioprosthetic heart valve relative to the abutment ring requires a torque exceeding a first rotational threshold selected based on a height of the at least one channel and a height of the at least one locking feature.

17. The method of claim 13, wherein the at least one ledge comprising at least one opening, and wherein inserting the removable bioprosthetic heart valve into the abutment ring comprises inserting the at least one locking feature through the at least one opening of the locking system.

18. The method of claim 13, wherein the locking system comprises a recess and the at least one locking feature comprises a boss configured to engage with the recess, and wherein, a torque required to rotate the at least one locking feature from the disengaged position to the engaged position is less than a torque required to rotate the at least one locking feature from the engaged position to the disengaged position due to the engagement of the boss and the recess.

* * * * *